(12) United States Patent
Vitek et al.

(10) Patent No.: US 6,255,473 B1
(45) Date of Patent: Jul. 3, 2001

(54) PRESENILIN-1 GENE PROMOTER

(75) Inventors: Michael P. Vitek, Apex; Noriaki Mitsuda; Allen D. Roses, both of Durham, all of NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 08/920,422

(22) Filed: Aug. 29, 1997

(51) Int. Cl.$^7$ .......................... C07H 21/04; C12N 15/00; C12N 15/63; C12N 5/00
(52) U.S. Cl. ..................... 536/24.1; 435/320.1; 435/455; 435/325.1; 536/23.1
(58) Field of Search .............................. 800/2; 435/122.3, 435/455, 320.1; 536/23.1, 24.1

(56) References Cited

PUBLICATIONS

Sorbi, S., et al. Missense Mutation of S182 Gene in Italian Families with Early–Onset Alzheimer's Disease, *The Lancet*, vol. 346, pp. 439–440 (Aug. 12, 1995).

Rogaev, et al., Analysis of the 5'Sequence, Genomic Structure, and Alternative Splicing of the presenilin–1 Gene (PSEN1) Associated with Early Onset Alzheimer Disease, *Genomics*, vol. 40, pp. 415–424 (1997).

Tsuda, T., et al. Failure to detect missense mutations in the S182 gene in a series of late–onset Alzheimer's disease cases, *Neuroscience Letters*, vol. 201, pp. 188–190 (1995).

Sherrington, R., et al., Cloning of a gene bearing missense mutations in early–onset familial Alzheimer's disease, *Nature*, vol. 375, pp. 754–760 (Jun. 29, 1995).

Sherrington, R., et al., Alzheimer's disease associated with mutations in presenilin 2 is rare and variably penetrant, *Human Molecular Genetics*, vol. 5, No. 7, pp. 958–988 (1996).

Rogaev, et al., Familial Alzheimer's disease in kindreds with missense mutations in a gene on chromosome 1 related to the Alzheimer's disease type 3 gene, *Nature*, vol. 376, pp. 775–778 (Aug. 31, 1995).

PCT/US98/17905 International Search Report, dated Dec. 30, 1998.

Database GenBank on LOCUS . Mitsuda et al., Transcriptional Regulation of the Mouse Presenilin–1 Gene, *J. Biol. Chem.*, 272(38):23489–23497. Direct Submission. GenBank Accession No. AF007560, Jun. 9, 1997.

Sherrington et al., Cloning of a Gene Bearing Missense Mutations in Early–Onset Familial Alzheimer's Disease, *Nature*, 375:754–760 (Jun. 29, 1995).

Mitsuda et al.; Transcriptional Regulation of the Mouse Presenilin–1 Gene, *J. of Biological Chemistry*, 272(38):23489–23497 (1997).

*Primary Examiner*—Deborah J. R. Clark
*Assistant Examiner*—Janet M. Kerr
(74) *Attorney, Agent, or Firm*—Myers Bigel Sibley & Sajovec

(57) ABSTRACT

An isolated DNA molecule that directs neuron-specific transcription of a downstream heterologous DNA segment (a promoter segment) in a mammalian cell is disclosed. The isolated DNA molecule contains a promoter segment from the mouse genomic Presenilin-1 DNA, or a DNA sequence that hybridize to such DNA and directs neuron-specific transcription of a downstream heterologous DNA segment in a mammalian cell. DNA constructs comprising such promoter segments and various uses thereof are also disclosed.

10 Claims, 11 Drawing Sheets

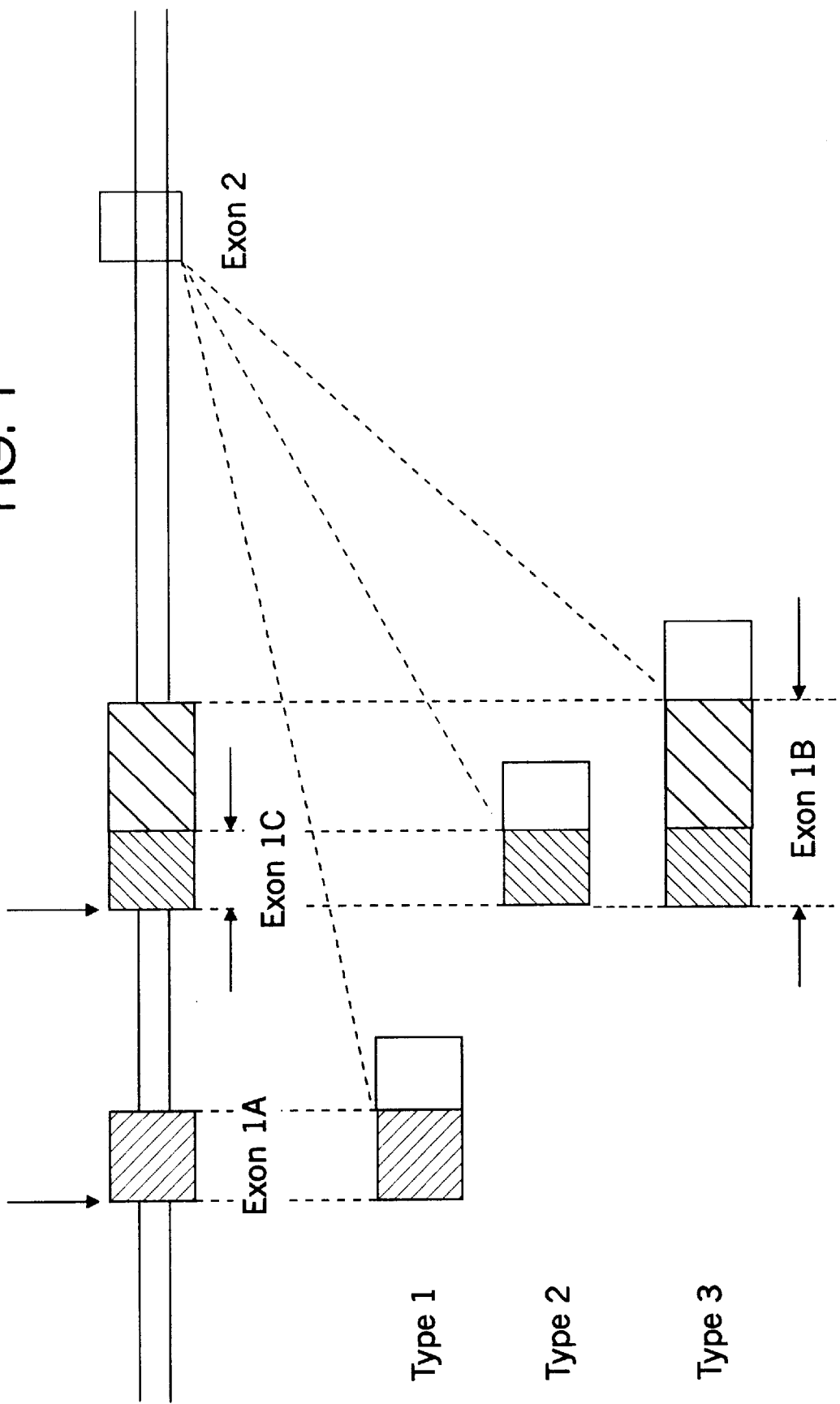

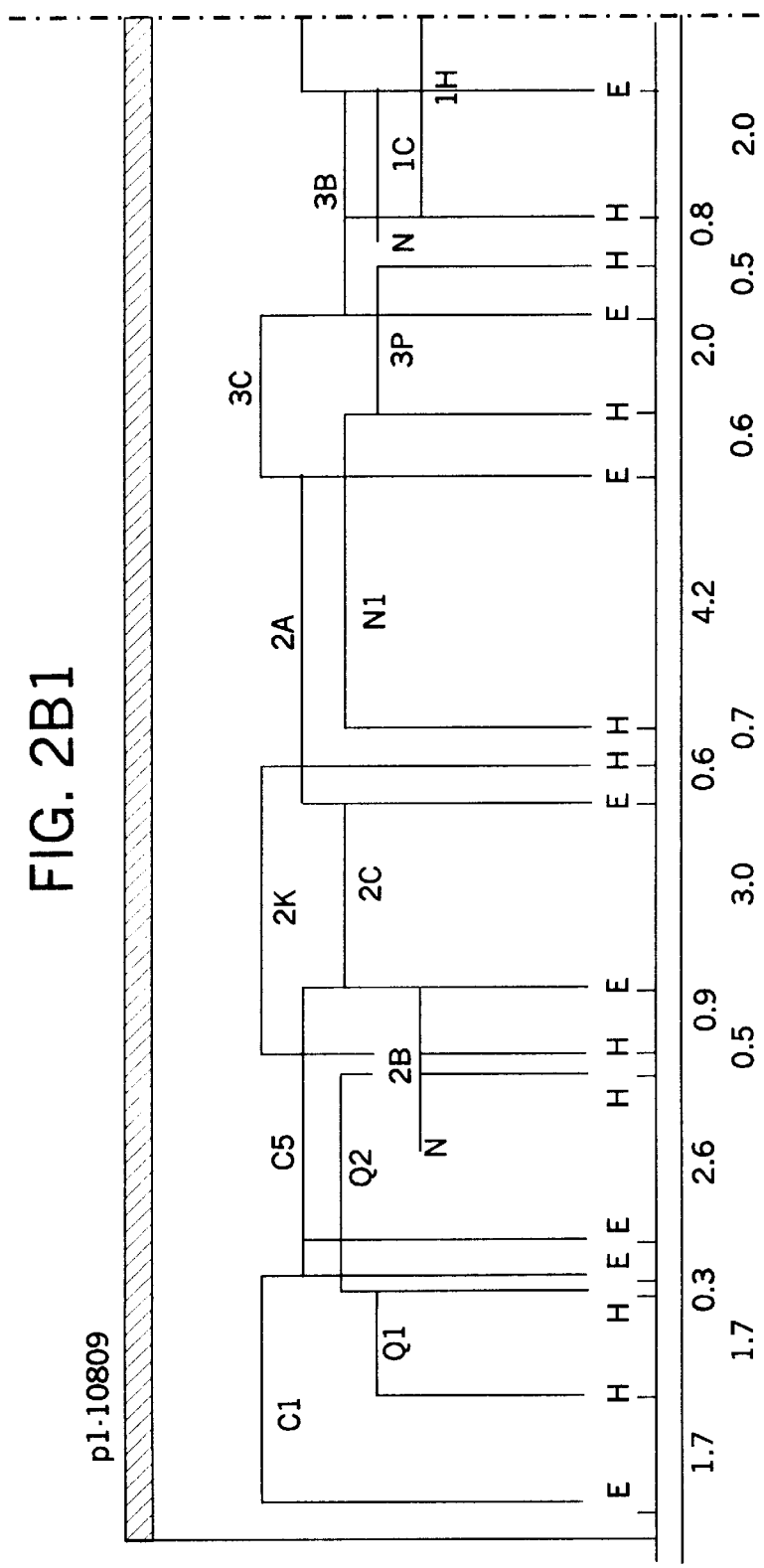

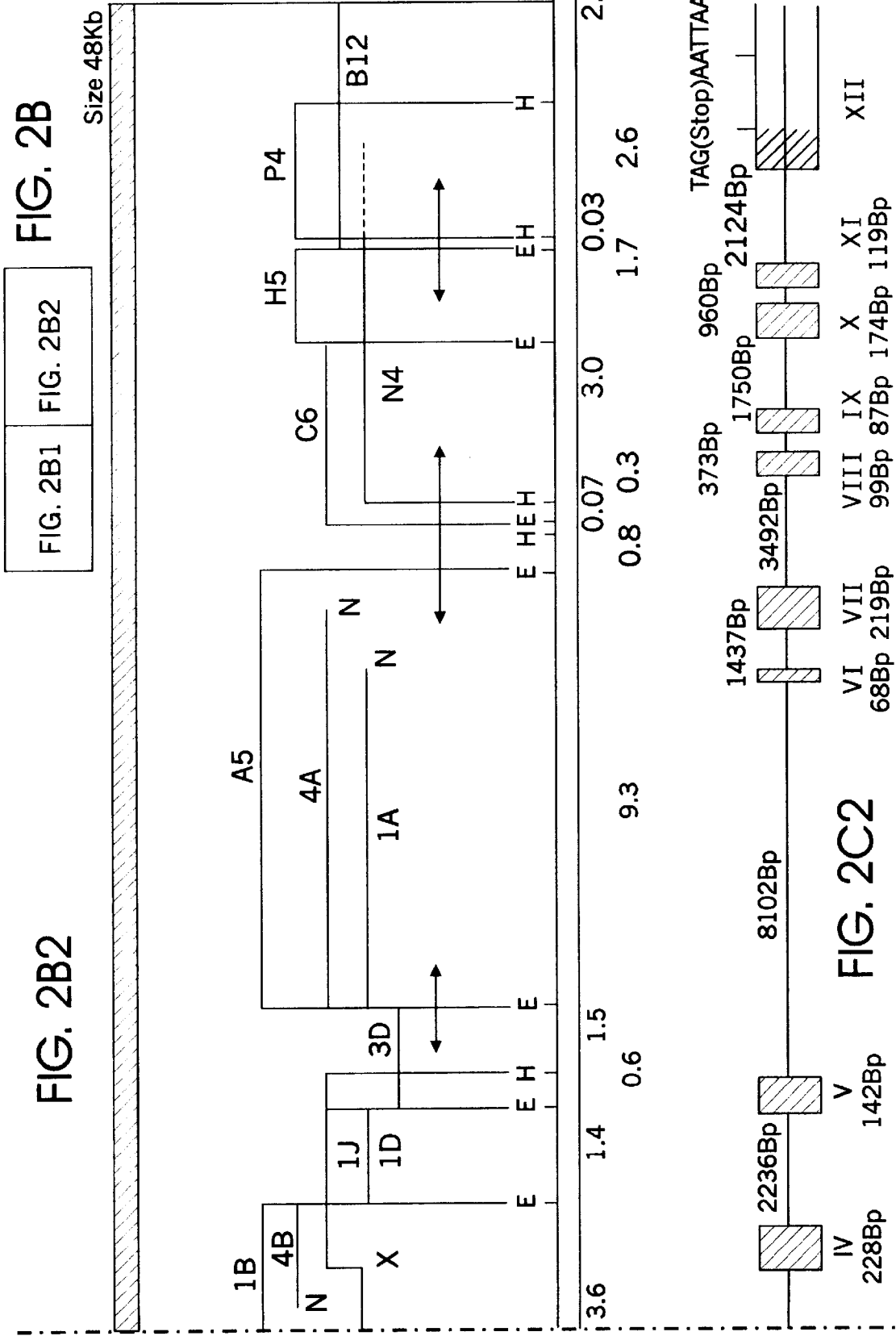

FIG. 3 mouse PS-1 promoter → Exon 1a

```
                                                          +1
PS-1 mouse   -39  CCCCTCCCGGGTCTAGGGGCCAACGTCGCCGAGGCCGGAAGTTG  +4
                  | |||||  ||  |   |  |||||||| ||||  ||||||||| |
PS-1 human   -39  CTCCTCCGTGGGCCGGCCGCCAACGACGCCAGAGCCGGAAATGA  +4
                                                    Ets1  +1

PS-1 mouse   +5   CGACACCGGTGAGACCTCTAGGGCGGGGCCTAGGACGACCTGCT  +48
                  |||||  ||||||||    |||  || ||||||||||||| ||||     |  |||
PS-1 human   +5   CGACAACGGTGAGGGTTCTCGGGCGGGGCCTGGGACAGGCAGCT  +48
                                        Sp1

PS-1 mouse   +49  CCGTGGGCCGCGAGTATTCGTCGGAAACAAAACAGCGGCAGCTG  +92
                  |||  || ||||||  |    |  ||||||||||||||||||||| | |
PS-1 human   +49  CCGGGGTCCGCGGTTTCACATCGGAAACAAAACAGCGGCTGGTC  +92

PS-1 mouse   +93  AGGCGGAAACCTAGGCTGCGAGCCG  +117
                  ||  |  |||||    |||  |||  |||  |||
PS-1 human   +93  TGGAAGGAACCTGAGCTACGACCCG  +117 mouse Exon 1c

PS-1 mouse   +439 GGCCTCTCGATCAGAGTGGAGCTAGAGATAGAGGAAGCGCCCTA  +482
                  | | |||  |     ||||||||    ||||  |||||||||| | |
PS-1 human   +441 GCCGTCTGAACTGGAGTGGAGTAGGAGAAAGAGGAAGCGTCTTG  +484

PS-1 mouse   +483 GGCTGGGTCGCCTTGAGCAACTGGTGAAACTCTGCGTCTGGTGC  +526
                  ||||||||   |||||||||||||||||||||||  |||  ||    ||
PS-1 human   +485 GGCTGGGTCTGCTTGAGCAACTGGTGAAACTCCGCGCCTCACGC  +528

PS-1 mouse   +527 CCCGAGTGTGTCATAGTCCAG  +547
                  ||||  |||||||| |  ||||||
PS-1 human   +529 CCCGGGTGTGTCCTTGTCCAG  +549
```

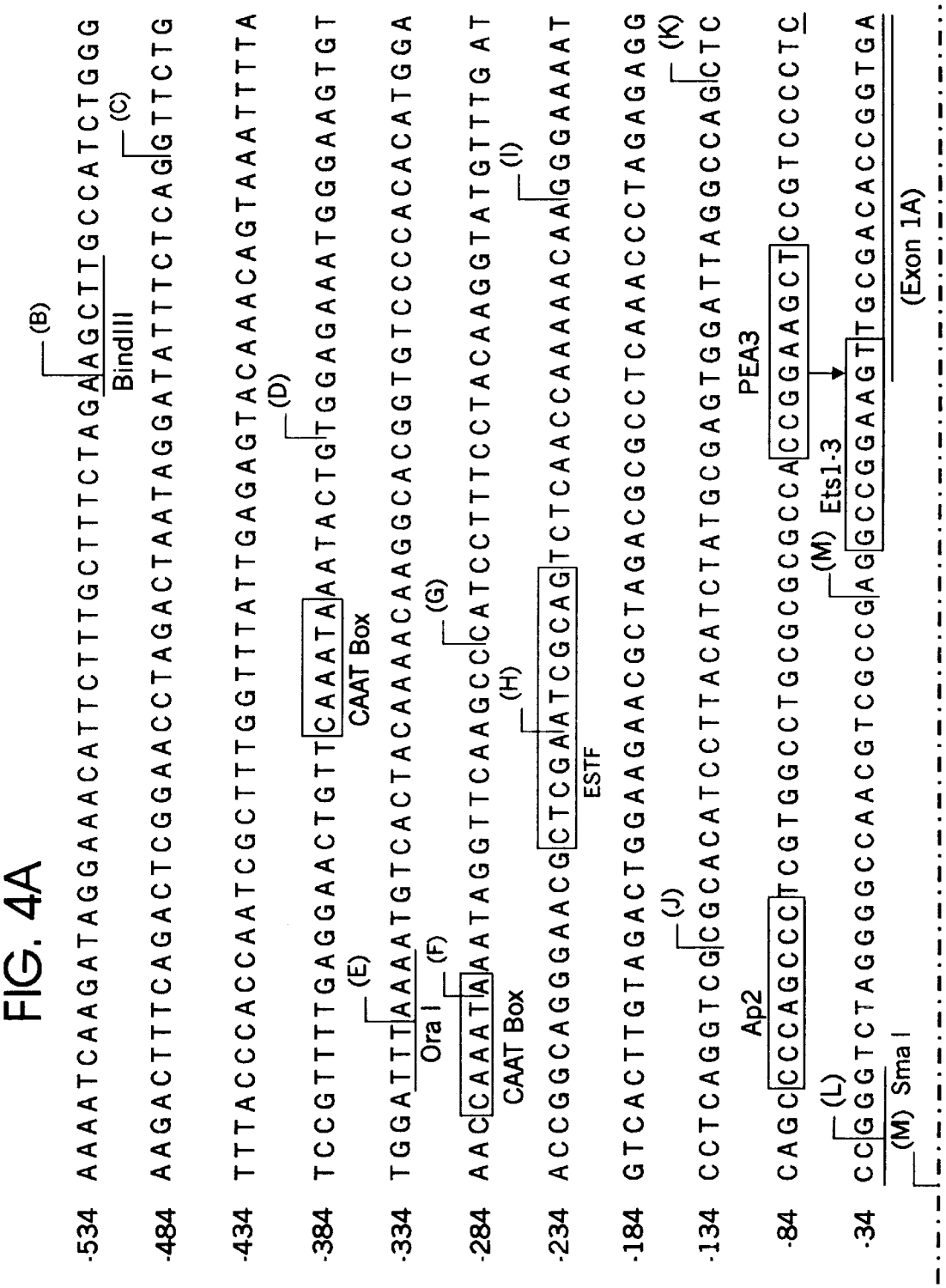

```
          Sol
+17   GACCTCTA GGGG GCCTAGGACGA ACCTGCTCCGTGGGCCGCGAGTATT
                              (O)
                              (P)
+67   CGTCGGAAACAAACAGCGGCAGCT GAGGCGGAAACCTAGGCTGCGAGCC
         Sol                                         Sol
+117  GG CCGCCC GGGGCGGGAGAGAGAAGGTGCGTG CCCAGGGTGTGC GGGGCG
                                      (Q)
                                      (S)
+167  G AGGGTGTCTCTGCCGGTCGT GTTCACCGTCGCGCCTGCCGGGGCGTCTCTAGGGATGA
                            (R)
         Sol
+217  GGGCGG GCCTGTGTCTCCGAGGGCCCGAGGAACCC AGATCGAGGAGGAACCC
                                         Sol
+267  G GGGCGG GGTCCAGGGC CCCAGCCGG GAAGT CGCGTGGG AAACGG
                                 Ets1-3                Ap2
                         Ap2
+317  GGTGAAGCCGGTTTCTCGGAA CCCAGCCGG GCTGGCTTCCCC GGGCGG CCGGGA
                                                  Sol        (Exon LB)
+367  TCTCCGAGCTTTCGTACC CCGGAAGT GCTGGCTTCCCCGATCAGAGAGCAGCCT
+417  GCAGATGGCTGGCATCAGGGCCCTAGGCTGGGCCCTTGAGCCTTGCGCTAGAGA
+467  TAGAGGAAGCGCCCGAGTGTGTCATAGTCCAGAAGTGAGTGGAGCTAGAGA
            (T)
+517  CG CTGGTGCCCCGAGTGTGTCATAGTCCAGAAGTGAGTGGCACTC
```

FIG. 4B

| FIG. 4A |
|---------|
| FIG. 4B |

SEQUENCE LISTING

```
<160> NUMBER OF SEQ ID NOS: 22

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 1
aggccggaag ttgcgacacc ggtga                                          25

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 2
```

-continued cggagagaga aggaacaaac                                              20

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 3
tcagctcttc gtcttcctcc tcatc                                        25

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 4
gatcacagtc taggttgctg gtgtg                                        25

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 5
tggggcaagg gacacaaata ag                                           22

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 6
tggctcaggg ttgtcaagtc                                              20

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence:primer

<400> SEQUENCE: 7
ccatcctaat acgactcact atagggc                                      27

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 8
caaacctctt gggattcttt c                                            21

<210> SEQ ID NO 9
<211> LENGTH: 23
<212> TYPE: DNA
<213> ORGANISM: Artificial Sequence

```
<220> FEATURE:
<223> OTHER INFORMATION: Description of Artificial Sequence:primer

<400> SEQUENCE: 9
actcactata gggctcgagc ggc                                              23

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 10
aagacctcga agggctgctg tc                                               22

<210> SEQ ID NO 11
<211> LENGTH: 9
<212> TYPE: DNA
<213> ORGANISM: Artificial Sequence
<220> FEATURE:
<223> OTHER INFORMATION: Description of Artificial Sequence:primer

<400> SEQUENCE: 11 gccggaagt                                                               9

<210> SEQ ID NO 12
<211> LENGTH: 7
<212> TYPE: DNA
<213> ORGANISM: Artificial Sequence
<220> FEATURE:
<223> OTHER INFORMATION: Description of Artificial Sequence:primer

<400> SEQUENCE: 12 gggcggg                                                                 7

<210> SEQ ID NO 13
<211> LENGTH: 8
<212> TYPE: DNA
<213> ORGANISM: Artificial Sequence
<220> FEATURE:
<223> OTHER INFORMATION: Description of Artificial Sequence:primer

<400> SEQUENCE: 13 cccagccc                                                                8

<210> SEQ ID NO 14
<211> LENGTH: 12
<212> TYPE: DNA
<213> ORGANISM: Artificial Sequence
<220> FEATURE:
<223> OTHER INFORMATION: Description of Artificial Sequence:primer

<400> SEQUENCE: 14
ctcgaatcgc ag                                                          12

<210> SEQ ID NO 15
<211> LENGTH: 6
<212> TYPE: DNA
<213> ORGANISM: Artificial Sequence
<220> FEATURE:
<223> OTHER INFORMATION: Description of Artificial Sequence:primer

<400> SEQUENCE: 15 gggcgg                                                                  6
```

```
<210> SEQ ID NO 16
<211> LENGTH: 6
<212> TYPE: DNA
<213> ORGANISM: Artificial Sequence
<220> FEATURE:
<223> OTHER INFORMATION: Description of Artificial Sequence:primer

<400> SEQUENCE: 16 ccgccc                                                                 6

<210> SEQ ID NO 17
<211> LENGTH: 48974
<212> TYPE: DNA
<213> ORGANISM: Mus musculus

<400> SEQUENCE: 17
gaattctggt catatgcaaa tattacttac cttggagtca ttgttaggaa aacctggcct        60
gattgactag gtcctggctt ctagtgactg cattcctagt cttgccttgc aggctcctct       120
cctaagtgac ctagtcaatc aggccaagtc atttcctgct tcactcatta gttgctactg       180
ggttttctca tcttcctatt gccaggtttt gaataatggg gaaaataaat gctacactgc       240
agaaattctc actattcttt ggcactgttt ggtcattctt aggttttagt gtttctagac       300
cctcaatgct atattacatt gaaaaaatag aaaattattt agtatgtgcc tttcaaatgt       360
ctcagatctt attcacatag ttagaagtgt tgtgtgcctt gatatttccg tgggtgcccg       420
agtgggatac attagcttct cttggcactc tataaacatt gtctgtctat ttgatattca       480
ttggtggtta atgtttaatc acctttgccc ttccctggtg tcagtcttcc catgtcattt       540
atgtaatatt tgtgtttata tccctaaaaa ggaatataga aaacagaagt atctgtagtc       600
tactcagttc ctgtccccc tccccttga gggtttactt ttacaagaat ctattggaac         660
actgagtgta aatacaactg ccattttgt ccattagaca gttctcttgc tcatagcttt         720
cattcatgag tattttttt aagatttatt tatttattat atgtaagtac actgtagttg         780
tcttcagacg caccagaaga gggcgtcaga tctcatggtt gtgagccgtc atgtggttgc       840
tgggatttga actcaggact tttggaagag tagtcagtgg tcttaaccac tgagccatct       900
caccagcccc attcatgagt tttataacct aggtgaacta agatttgttg taggacagtg       960 agatttttt atatatatac cagtactcca cgaacatctt tgcacaaaaa tgtttgtcga      1020
aattgcttct ctgtatagtt tacagcattt gccattctac caaaagatcg caattaatgt      1080
agtttgcaaa tggcttttag tctatgcttg tttagcaagt gtattgagct tgttctgtac      1140
tgtctacaat tttctgcctt cttcccatat aagtaaatga ttgagggtat aagtaaatga      1200
ttgagggaaa actacccaag gttatgctat gtctcctccc agttgccatt ccgctggcgg      1260
aaaagactaa agtatcaaga tcttaagcat gaaaatagtg aagtctgagt ttattgaagc      1320
agggttgaga atgttgggag aaaatggaga tggatgctct actatttaga acgaggcctt      1380
ctgggaagta gaaaaaagga agtttgaccc agtgtatctt agtttgacct gtaatttggt      1440
aggaatccca gtccgatttc aactcactgt cctgccccat ctcctcctga gtgttatgat      1500
ttcagataca acaccatccc gatgtatttg tctctgttgg gagtagaatc tagttcctcg      1560
tgtgtgctcc ttaagcacat tagccgtttt ctggttattt gggattatga ataatttctc      1620
tgttgttttt tgcccaagtg aaatgtgtgg tgtgctgttg ataattgtct ctccgattaa      1680
ggaaaatctg agggatgtaa aaatcaagat aggaaacatt ctttgctttc tagaagcttg      1740
ccatctggga agactttcag actcggaacc tagactaata ggatatttct caggttctgt      1800
```

-continued

| | | | | |
|---|---|---|---|---|
| ttacccacca | atcgctttgg | tttattgaga | gtacaaacag | taaattttat | ccgttttgag | 1860 |
| gaactgttca | aataaatact | gtggagaaat | gggaagtgtt | ggatttaaaa | tgtcactaca | 1920 |
| aaacaaggca | cggtgtcccc | acacatggaa | accaaataaa | taggttcaag | cccatccttt | 1980 |
| cctacaaggt | atgtttgata | ccggcaggga | acgctcgaat | cgcagtctca | accaaaaaca | 2040 |
| agggaaaatg | tcacttgtag | actggaagaa | cgctagacgc | gcctcaaacc | ctagagaggc | 2100 |
| ctcaggtcgc | gcacatcctt | acatctatgc | gagtggatta | ggccagctcc | agccccagcc | 2160 |
| ctcgtggcct | gcgcgcgcca | ccggaagctc | cgtcccctcc | cgggtctagg | ggccaacgtc | 2220 |
| gccgaggccg | gaagttgcga | caccggtgag | acctctaggg | cggggcctag | gacgacctgc | 2280 |
| tccgtgggcc | gcgagtattc | gtcggaaaca | aaacagcggc | agctgaggcg | gaaacctagg | 2340 |
| ctgcgagccg | gccgcccggg | cgcggagaga | aaggtgcgt | gcccagggtg | tgcggggcgg | 2400 |
| agggtgtctc | tgccggtcgt | gttcaccgtc | gcctgcctgc | cggggtccg | ggcgggcctg | 2460 |
| tgtctccgag | ggccgcgctg | cgggcgtctc | tagggatgag | gggcggggtc | caggcgggcg | 2520 |
| gagatcgagg | aaccccgcgt | gggaaacggg | gtgaagccgg | tttctcggaa | cccagccggg | 2580 |
| gccagactga | gagcagcctt | ctccgagctt | tggtaccccg | gaagtgctgg | cttccccggg | 2640 |
| cggccgggag | cagatggctg | gcatcagggg | tggcctctcg | atcagagtgg | agctagagat | 2700 |
| agaggaagcg | ccctaggctg | ggtcgccttg | agcaactggt | gaaactctgc | gtctggtgcc | 2760 |
| ccgagtgtgt | catagtccag | aagtgagtga | gtggcactcg | gggctaactt | ctcagtgtgt | 2820 |
| ctgttggcag | gcgaagagtc | gtatggcgct | tgttctttct | tcagaactgt | cacgatgcat | 2880 |
| gtgtctgacg | cttgtaggcg | cctttagtgt | ttgctagttc | ttcccttca | cgttttcaaa | 2940 |
| tgtggcactg | ccgcgaacag | aggctcaggc | acatccgcct | ggtagtggag | gacggagtgc | 3000 |
| atgagacaat | tgaggtaact | ttttacataa | ctaggagaaa | tgagagttcc | agtaacagaa | 3060 |
| acgtagaaga | aacgtgagca | ggacaggcga | tctgttcaac | taacgcataa | gattgactgg | 3120 |
| gttcaagttt | ggagaatgag | agagaaataa | ggaagttagg | cagtggtttg | gaaatagtac | 3180 |
| ttttgaagtg | acagcgggtg | aagatggcct | gaggtcagag | ctgtaaactg | taaacatggg | 3240 |
| tcacttaagt | agatttgctg | tttgatgttg | gagcagagaa | ctgggtggac | acttagggaa | 3300 |
| cacaacaaag | agccaggtag | aaggaggaca | acgaggctgc | tgaggaggac | gaatgcagaa | 3360 |
| accacaatag | tgcagtgtca | cagaagctga | gaaacacgga | agcttcaggg | agcattgtca | 3420 |
| gcgataggaa | tgaaaggcct | ggtgttgttt | tagaaggatc | tctgtaccat | tgtacccttg | 3480 |
| aaagatgagc | gtgaaccaca | aatactagtt | ttaaatgttc | ccacagacac | ttttttaaaa | 3540 |
| aatttttag | aggtttattt | atttattata | tgtgagtaca | ttgtagctgt | cttcagacac | 3600 |
| cccagaatag | ggcatcagat | ttcattacgg | atgtttgtga | gccacaatgt | ggttgctgga | 3660 |
| atttgaattc | aggaccttca | gaagagcagt | cagtgctctt | aacagctgag | ccatctctcc | 3720 |
| agccccacag | acacattttt | aaaggtaaca | agaagcagtt | gaaattagtc | ttaatgattt | 3780 |
| gttaatccag | tgtagctaac | agtttcattt | ttaacaggaa | atccgtgtca | aattaacttg | 3840 |
| tcctctctag | atagttagga | ggctcttcag | tgaccagaag | caaccctga | ctacagtatc | 3900 |
| cccagcacct | ggcacagtgt | ttccttgtct | aaaagaaacc | tgattcctat | ttgctgctcc | 3960 |
| aagaatccct | atttggtttt | cagatgtctt | ttccagttcc | ttgtttgagt | gaaagcagaa | 4020 |
| agaatttatg | caagttaatt | agatgtaaat | attcgttttt | aatttaaaaa | tacttgtatt | 4080 |
| ccatccattt | ccacagaagg | tagagacatt | gactcacaat | gaaaataact | tcattacaga | 4140 |

```
attattaaaa taactttggg ttgagttttt ataatttcca ggtataggcg gtgctttagg      4200
agtcccagct acttggaagg ctgagctgga aaatcacggc cagcctggat aacagagatg      4260
gtgaatgact cgagagtaga gcgaattcat ccacctgatc taacctagga tggcctgtag      4320
tctgtttgac agtacagata gagaccatgt tgagtcttat tctgtgggtg tgatatgtat      4380
gtgtgtgcac ctctactta tatgcaaagc tgaagtcttt gcctatatgc tcacaaattc       4440
agaggccaga ggaggacagg gggagcgttt ctccactgtt tattgcctta cttaaaaaac      4500
aaaaatgtta tttttgtgtg cagggttggg ggggcttcca tagtaatatt cggaagtctg      4560
aagttagctc tctcttccca cctttatatt agtactgggt actgagcata ggtctccggg      4620
tatgtgggac aagtaccttt actgtctgag ccatctcgag agtctccccc cacccccacc      4680
cccaccccg ccccctgggc cttttattt aattttgtt gttgttttgc ttggttttgt         4740
gagacaggga ctctctgtgt agccctggct ttcctggaac tcactatgta aaccaggctg      4800
gcctgaagtt cacagagatc tgccaccaca cccagcttaa ttttaaaaa cttaattgtg       4860
tgtgtgggag cacgtgcgcc atggcacaca gatgttataa cacacatgat cactttatgg     4920
aatccttttt gtttacgata tgtgggcgct ggggattaaa ttctgcttgt cagacgcggg      4980
ctgcaccatg agcaccaatt ttattttata aggcacagtc tctttattga gccgaagctg     5040
tttcagctag gtgggctgtc tgtcagtctc ctgggagcct cttgtctcca cctcccagtg     5100
ttaggactgt aggcgcagga actatgcctg gcttggatgt gatgctggga atttgagctt     5160
tgctcctttt gacagcaagt gcttttaccc actgagctaa ctccctagat cctactgtct     5220
tgatatactt tgagactgtt ggtgtgtttc accatagacc taaatggata ttaattactc     5280
ttgtgattct aaggctctcg gatgtactat tgagcatata ctgcctttac agaatccaaa     5340
agaaaatcca tattctaaat acagttaatc ctgaaggttt gaaataaatt atgagctgat     5400
tttagctcat gttcattgtg tcttgtgagc ccgccagttt taccattgct ttgaaataag     5460
ttgcagcaat aagtctccat agcagagctc caaacctcac agcttagagc acttaagtta     5520
actcagggct ctgcttcagg gtggaatgtg tggctcagct gggaccattt tgatttgagc     5580
atcttctcct ggggcccagg ttgaggggac aaaaactatc aaaccactct gctgacttct     5640
caaggcaagg acagctgcac aagcatggct cacatatatc tgccagtgtc catcagctaa     5700
aattgcattg ataaaggcac agtataggag ctcacataaa gacttaaaat aggtgatggc     5760
tgttacccag aaagagacca aagagcaatc tcagggaatt ggttctagga ctactagttt     5820
ccaaaatctg aggatgtccc agtccttaca tttaacagta gtatttgcgg gtaagagtgt     5880
agtcatgttc agagaccttg cttgattcct aacactgaag aaaaaatatg aaccaaaaat     5940
aaatatatta tttataaatc ctccggtgta ctttaaatca tctctcaact ataatacccca   6000
ctaatgtaaa tgctgcgtaa ataatcctta cattgtgttg attatgaaga acaatgaaat     6060
ctacgtgcca aatgttttca gtctacagtt gatcgactcc aaggatcctg aattagaaga     6120
tatgaagggt aaccgttctt cccttgggga gactggtgga aggagaggat atttactgaa     6180
taataattgt ctctaccaca gatggttcgc agaggtggag tgggatggaa agagggaaaa     6240
agccaccctc aaccggctgc atcactgccc ttgctccttt tagttctgtt actttcagaa     6300
catgtcttgt agggctgggg gaatgcttcg ctcgctctct ctgccttatg gatcatgggt     6360
ctgtcttggg tattcctaag tcaagttctg gaatacagtt gagggtttgc ttacattcac     6420
tgtggttatg agaagcccag gtagaacagg gtttgatggt acncacttgt aatcctggca     6480
ctcaggagtt ggagtcagga ngacctcaag cacaagcatc gtgagcaaga cctgtctcca     6540
```

```
taaatgcaga aacaccaggg cgcacccttta acaacagtgc acaggaggaa gaagtacgag    6600
gacctctgag tttgaagcca gcgtgatctt catagcaaat tgctgcccag ccatggttac    6660
attctgagac cctgtcccaa acagacagac agccaacgag agagatggca cttagtggca    6720
ggacactttc caagcatctt tgcttcccac caaccaaaat aagtaaatca aaattcaaac    6780
tctaatcaga gtttgagttc cctatcaggg agataagtag gaaaaactgc gtggggcgcg    6840
ggagggtgtg gagggtcctg gaagagagga acagcctgtt tgtgcagtct gcctgtcagc    6900
tgtgatacct ggccccagct ttcatgataa agctttagtt tgtttgacag gcaaccttga    6960
gatcatgggg ctttcggcag actcaaaggg cggagagatg agggagtaaa caagaaaag     7020 ctgggtcttg agaactcttg tcctctgaga gtcagaacgc cacttggtgg gatgaagtgc    7080
catgttacca tgaatatgtc acccacctcc caaacttcca tcatgacgtc tttaagtctg    7140
cagctcagaa cagagcccac tattctgccc ctctgccttt tcttgtaggc ccctcagctc    7200 tctcttttgga gtatgtgcct tgctaataaa cttctgccta gactacatgt ctgtgtctag    7260
tctgagtctt cttcttcccc acttcaagac aggaaatgga gtcntcactt caggccatgg    7320
cggcagcagc ctgattggta ggaaaataaa tcaagagctt gaaaacgtta tttatttatt    7380
tatttatttc ctgcctcaca ccttgaaagc ttttttagcac tatagccatt tatgtagagc    7440
aaaaaaataa ttttggtagt ttttaaagtg gtagaagctg ggtaagtggc ttagggacat    7500
tccgccacag gctctttgtg gtgataaagc catgcttatg tctcactgaa gatgttttgt    7560
agtgtaccag ttttatttac atttgtctca agagttagaa aatgagttca gtgtacagtg    7620
agatgggaga aagtacctgt tggctttttt gggggtgag agagttcgag acagggtttc    7680
tctgtgtagc cctggctgtc ctggaactca ctctgtagac caggctggcc tcaaactcag    7740
gaatccgcct gcctctgcct tccaagtgct gggattaaag atgtgcgcca ccactgcccg    7800
gctagaaagt acctttttgt gtttgttttt tttttctttc ctttaaaatt gattaaattt    7860
caattaggtc tcttgtagct caggctagct ttcagattta actttgtagg caaagatgat    7920
tttgaagttc tgaattttcc tgcctaacat tctttctaag tgttggaatt aacaagtgtt    7980
tcaaacccat actggtttgt gtttaaggag attgaagcta gggcttggtg tgtgctaaac    8040
aagtactcta tgaaccaagc tacatctcca atgctgtggg tgctttagtg aatgggaatt    8100
tcttttagga acctattctg aaactttaaa cattgctcct gagatgtttt agaagttttg    8160
gtgttgagag gaggttttct agctggatgg attttctttt ttcctccgct acgtgggtgt    8220
gtgtaacatg ggtgtgtgct ggaggctgta gagtctttct ggttcactct ccacttcttt    8280
cactgagcta tgggtttagt caaacccaga actcactaat atagcttgtc tggccagcca    8340
gcttgctttg gggaattccc agtttctgcc tctgtgttct ggaattagag acaagccacc    8400
agagccaccc agtatttagg tacgttctga ggaatcgtat atccagtcct cacattgcat    8460
aaccactgag ccatctctcc agaccctgca tcggcttctc tgtggagcac atctaaagct    8520
gtgagattac tcataggctg tggcttttcc ttcccttgta tctctgcttt tggtttcccc    8580
aatgctaagg atggatccca gggtctgcac atgctgtgca agcactctgt cacagggctg    8640
catcccagct cctagtcttt gtctgataga aattgccatt gctcatcaaa acaatgactt    8700 cttttttcctt tgcccgactg cccaaattgt tgtgcttgga gcaagcacaa agcagagggt    8760
aaagaagcat ttatcagatc agaactgata ggaaagttct agtaaagaaa atacattgtg    8820
ggcagaaaca ggtggcgtcc ttaaaaggga atggcgtctg tttatagcag tcaagagaca    8880
```

```
cattgcctgg ccttaccttt tgagctattt gtatgaggtc caatttgatt aagtaagagg    8940
tagtctgctc attgtcttgg gtaaatgtat agattggccc tgtcaggtaa ggtcctccgg    9000
acattgggag ttagtcttat tgtgtatatg aggttagcag cacagctgca tagctaggat    9060
ctgattgtta gtgagcattt tggtttttta ctgttgtccc ttttggcctc ctcatctcca    9120
cacaagtgtc tgaaagagag gagctaaata tcaggaaggt gttgcggtgt gtccgtcttc    9180
agtggctgtc caaaaagaaa agcaccaaaa tctatatccc tttccctcct ccctctgcca    9240
tccaggtctc tagtcagcta ctggcttctg gtgttcatag ctctcagctg aaaatgttat    9300
caactttgca agtgtcttct gccatgctgc ctgggcagtg gggtattgac cttttccagt    9360
gatggttttg gctgttgtta aatccgaatc aactccgttt ggtctacccc ctttgtccca    9420
ggagtgtgtg cttgttccat gacctggcca tggcctgctt ctgcttcggg gcttattcct    9480
tctgatcata ttccatcagg ctcttcctgg gatcgtgtga tttctctggg tgagcagagg    9540
accccggctg agtgtcctca ccacctggaa tctggattgg gggtgttact catttgcccc    9600
ttaaccctgc acaggcacat tgcctcacct tgatgtttat gacattcgaa cgcagagtct    9660
tctagagaaa aaattttggg gggggggggg gaggggtttg aaaggtaagg agaaaactcc    9720
ctgnaaccgg ggatagggga ttcaaaagag agttgtccct tttatttatt ttcagacatt    9780
tttgtagatt tatgtgtata agtgttttgc ctgtgtgcat aaatgtacac atctgtgtgc    9840
ctggtgcctg tggaggtcag aagaagacac cagatgccct gaaacaggag ttatgaatga    9900
ttatgagcca ccatgtgggt gctgggtagc aaacctgggt cctctgcaag agcagcaagt    9960
gctctgtaac cactgagcca antgcagccc cntcccccaa ccccaccccc accccaggg    10020 aactgtatta gggtttctac tgctgcggac aaaaacacaa tgaccgaaaa gcaagttggg    10080 gaaaagggt ttatttgatt atactgccag atcatactcc atcgttggag gaagtcagga    10140
caggaagtca agcagggctg gaatctggag gcaggagctg atgcagaggc catggaggga    10200
tgctgcttac tggcttgctc ccagaaccca ggaccaccag ctcagggatg gtaccaccca    10260
ccttgggctg ggctctcccc tgttgataat aaattgagaa aatgtcttac aactcaatct    10320
catggaggaa tttcttcaac tgaggctcct tcctctctga tgactctagc ttttgttgac    10380
acacacacca caaaaccagc cagtacagga ataaaatttt gggggtgtgt gtggtttgtt    10440
tgggttttgt tgttgttgtt gttgttgttt ttagacagga tttctctgtg tagtcctggc    10500
tgtcctaaac tcggtctgta gcccagactg atcctaaaac tcagagatct gtcctgccta    10560
tgctactgag tgctgggatt aaggggggtgt gtcactattg cccagctccc atgggaactt    10620
ttttaaagag tcaaacagaa taatgattat gaaaagaact ttgaaaatag cattgggagc    10680
atgctaaagt gatgggtgtg ttattggtgg gtcttagagg atttgtccca gaacgcccca    10740
gtgtggttcc ttataatggc taaacaggct atgtgagcct gaaagaaacg acttaaagga    10800
cacagtccca cccattgtaa cttacctgtt aaaataaata cttggactgt ctgtgcagaa    10860
tctcaagttt ccttatatag tgggagcatt gatgttaaag atctcgttac tttgtaagca    10920
gtagttttgt agtaataaaa cgagtgtaat ataacctagt cggcattcct gtaagntcct    10980
agaggcaggg acgttgtttt gcaacagagt cctgtatgtg ggttaggatc ttttgatgcc    11040
agacagggta agatggttga cttttccttgt attttgagac agggtctcat tgtgaggcgg    11100
ctagctgctg tgcgtgcttg gattaaaggc atgtggcacc acgctcagcc actgattttc    11160
ttgtaaaatg gatgggtaaa gtgagcataa tacgttactt aaggtgttcc cactttctgt    11220
ttcaattttg catggaagga aggagaaaga tgaatatgaa agacagttta cagtggtctc    11280
```

```
agccctgtgc tcacctttgt cctgcccttc tccagggccg ggtgtggtgg catatgcctt  11340
taatcccagc actcgggagg cagaggcagg cggatttctg agttcgaggc cagcctggtc  11400
tacaaagtga attccaggat agccaggggc tacacagaga aaccctgtct cgacacccct  11460
ccccccccc accaccacta nccccagttg gcaggatgct ggaacagaca ggtatggtgg  11520
ttgatcactt ggagcactca ctgtaaaatg agttccttaa gttcaacctc tcagagacct  11580
gagaaggaca aattttacct gagtaagcag gaattgtaat ctaagtagcc taagtaacaa  11640
ttaaaatgac agacttaccc attgcccaga cagccactcc acctgaaaac agaagtagtc  11700
tttgcgtgcc cctctggccc tctgtggaga aggaacatga gatagaccaa cctaatcttg  11760
tcttaggcac catgggacaa ttagctctgg tgtctttgtc cacatttaca gcagtgtcct  11820
gacagggggtc aaggtactgg gacaaatatg gttggtgtag ccacaatcca ggtggagtcc  11880
ttcattgttg tgcccatatc ttggagacct tggagcaggg cactgctata ttttggaaat  11940
ctctgtcgtg atatatttaa gcatcttaaa tgccatattc agcaggtctc tgaagtgcct  12000
gaggaccgtc tgtctatcag aagtatatct gaacagacaa gctttgcttg tttctcctta  12060
tccatcttag gcttagcctt gaaaatatag acagatgggt agataaagtt tgaggttatc  12120
tgctctacac tgtacctgtg atgttagaat aaagtacctt ttaaagagtg aagcataga  12180
gcataagttt cagaatacaa aacccgtttt aacaagtgtt aacatgtaat gtctccaaaa  12240
ttaataccaa gtgtgttatt atatgtttca aggtttggtt gtcagggcca cccagcaagg  12300
tatgttgtgt ttgtttggtt ggtttgattt ggtttagttt ggttggtttt gttttatttt  12360
gttttcttga acccataaca gggttatctg ccagccatgt tcttgtcctt aatcaagatg  12420
gtggtgaagc catggttcca ccctctttat cccatggtaa agatggcaac cacttcgtaa  12480
tctttctggc agcgggtgat ttaagtagca gtctgctccc taccatcact gttgccagtg  12540
aggcagcaca tggacctggg ggctgtgggt tggggcggg gctaggtggc acctggagct  12600
gtgtgtgggg aggtggtcgg ctgctgaaac tgttgtggtc aagcgggcag gtgagaaggc  12660
ggttcacaag aattggaatt atggagttcc gaccaatttg gataaagctt tcaatttag  12720
atgcggtggc acccattttt ttaggctttg ccggggacca aaggctcaaa tgtacattgt  12780
ctgcacataa gcctggggtt atacagttgg ggttggggga ttagcctcag gtcaaatgtt  12840
tttgaaccca aggctccccc agaggctggc ttctgacaat ttgttttcca aggctgctgg  12900
gaggtggtta cacctggagt ccaaagtctg tcgcatcagg ggcagagaaa gatgggggaa  12960
aggagtggtc ccctattctc acgtggcagg ggcctcaact cctccagagt caggacacca  13020
gatgataagt ttttctccac tggtgaagtg agccaattca agccagagta aagtcaatta  13080
aggcaggttt attaggaaga agttctcagg tgggctcact ggtcctaaag tggggaagga  13140
gacagggag gagggagaga aagagaaaga acatgtgcac acaggagag agaaaatgga  13200
gaggggggcag aaagagacca aaatgtttgg attatgtagg agagcctctt ggggaccgga  13260
agcccgtgta gggactgagg aatgctggga gaacctggag gtcagttcct gtcttggtag  13320
ataaaatatg catatgaaat atgcacctca gctgtttgtc ccgggtctga atcccaacag  13380
gtacaagtga atttgactaa ttacgagtgg cttgataaaa ttctgctttta tacttaatcc  13440
aggaaccaac acaagacagc agcccttcga ggtctttagg cagcttggag gagaacacat  13500
gagagaaagg tttgttcttc cagaatgaaa ttcgtgagag tttaaaaaca aatgagccgt  13560
agccacctca aagcataaag tcttgttttc ccttttcaga atcccaagag gttttgtttt  13620
```

-continued

```
ctttgagaag gtatttctgt ccagctgctc caatgacaga gatacctgca cctttgtcct    13680
acttccagaa tgcccagatg tctgaggaca gccactccag cagcgccatc cggagccagg    13740
tacagtgtca gtgccggctg ctgctgaggc cggggcagct ttgctctact ttgccgaatg    13800
tcttttcttg ttaaacatta agctgagggg aaatgtcaca gccttggtgc tagggaccc     13860 caaactgcac ttgttttact ctgttctgcg ggggactta acctcatgtc accccaactg     13920
aaactttgcc catctgcatg atatgtaagg accgcatgct ccacgttatc tgtcttgaat    13980
gtactcttct ctaggaagaa gtgagtgcat tgttttatgt tttctagtgc tggccagttt    14040
ctgacagtgc tcggtaagta tttagtgacg gtgattatac aatgcaaggt aaactgctgg    14100
gagctcagga gagggtggg atacagggta tatacacaaa ctcttcacag accacacaca    14160
ctaaatctgt ctgttgtaac cctgtcagct aagcactact gactggaggc agactccaca    14220
gcaggcctag gagctgtcta gggaatcggt agaattttct gaggtacaac caagatggag    14280
ggaaaccttg acaaggccag tctcaggtct gcaagcctgc cttgtgtagt ttgtacttgc    14340
tagtgaaagc tgtcattaaa ggcaagtcac aagtgaggat tagggagcc tggagagatg     14400 gctcagggg tcaaagcaat tcctgctctt ccagaggacc caagatagat ccatatgagg     14460
tggctcataa ctgcctgtta actccagctc cagaggacct cttctagtct ctgagggtg     14520 tgtgtgtgtg tgtgtgtgtg tgtgtgcgca cgtgcgtgcg cgcgcgtgta tgcatcaaga    14580
ttgagcctta agactttctt tatactctga agatttagag ttcctcactt tcccatcagt    14640
aaattttaga taatttactg aataatctca gtacgctcct accttaaatg ttttgggagg    14700
accaggagtg ggaggagcct gtagctagaa tgtaagactt tgcattttaa aactgttata    14760
atcctgaaca agtagggtca agattaaagt ggttactcct accacaagta taataaatag    14820
aaatcatttt ggaaaagact aaccaaatcg ttcttagttg gcagtctcat gtaagtttaa    14880
tcaccattat ttgttggtag gtgacataat gaggagacca tgtaaaccct cttttgttcc    14940
acagatctct tgcctttacc atatccttgt aacctcttaa acagaggcaa ccacaggctt    15000
caggagtcca gaaaatagtg tcttatcttg ggctgctatg tattaatctt actaatggta    15060
aagggacttg atgtttgata ggtgatgttt tttaaaaccc aaagatttct aaaactgtta    15120
ttgtacaatg ttctaagcat ctaaagcagc ggttctcaac gttgctaacg ctgcaaccct    15180
ttaatacagc tcttcatgtc atggtggccc caatcataac attattttca tttctacttc    15240
ctaactgtaa ttctgttgct gttatgaatc ataacataaa tatcggatat gcaggatctc    15300
tgatgtgtga cccttgtgaa aaggttgtcc aaccccaaa ggggtcgcga cccccagctt     15360
gagaaccacc gatctagagt gtagcaagca aatacccaac tttattcaag ttggagactg    15420
tgttatttgg catataaggc aattttttt caccccgccc cggccctata aggcaatttt     15480
tattaagatt tttctgtgtc ggtgactttt taaaaaagat ttattatgta tgtgagtaca    15540
ctgttgttat cttccgacat accggaagag ggcacaggat gtcattacag atgattgtga    15600
gccaccatgt ggttggttgc tgggatttga actcaggacc tctggaagag cagtcagtgc    15660
ccttaaccgc tgagccatct ctccagcccc aatgtttctg tgttttaaaa gattttctaa    15720
tcaggaatgg aagtgatgat gcatgacttt aatcttcata ctcaggcaac agaggcaggt    15780
ggattctgtg agtctgaggc caggttacat gtttgtctgt acgagcatct catcactaga    15840
tggagtgaga tctgatgtgg gtgctgggac tgaacactgg tgagagttct taaccccctga   15900 gcttctctgc agccacaagg ggcgtgcagt ctgcctgtgg gtaattactg agaacgagtg    15960
cggtgcactg aggacttcag tgtacgtcgc tgctgtcggg acttcttaat gaaaagctca    16020
```

```
ctgcttgctc ttttttaatt tttttcagtg ttctggtaac catggctgtc ctggagcctt    16080
tcatgtagcc cacgttggcc tttatcttac catcatcctc ttacctcagt ctcccatgtg    16140
ttcagataaa ggcagagcta ccatgcctgt gaaaaacttc tgcctttaat ttctcttaaa    16200
ataacactat gtctaaacca ttttagtagt taataagatt tttaattttg gaaaccatgt    16260
atttttagta tcaactcatt ttaacagttt ttaaacactt ttgttttctc tttggttttt    16320
cgagacaggg tttctctatg tagccctggc tgtcctggaa ctcactctgt agtccaggct    16380
ggccatgaac tcagaaatcc aacctgcctc tgcctcccaa gtgctgggat taaaggcgtg    16440
cgccaacact acccgacaac acttttttct tttttgtttt ctaagatcgg ttctctttat    16500
gtagccctgg ctatactaga actcaaagca tattttacaa ctcctttaaa aagatactta    16560 aactttatttt tgtttatttt taaaagagag tccatcctac tgtgtagact ggactctggc    16620
ccaccggcct tagcttccca atgctggcgt gatgatcgac tgccactagg cccagtttgt    16680
tttgatgggg ccttgttgaa ttgcccagac tggcctcaat ttcaagatct tcctgcctca    16740
accagaaagt attagcatgt actactgtac ctcgctgaca gtctttaaga atggctccat    16800
tgtggaataa ttgccatatg gttaactata catagaggat tcaatgtgat gactttttttt    16860 ttttttttaa ttttcaagat aaggtttctc tgtataacag tcctatctgt cctggaattc    16920
actctgtaga ctaggctggc ctcgaactca cagagaccca cctgcctccc aagcactggg    16980
attaaaaggt gtgcaccacc acttctggct caatgcgatg acttatagca tgcataaata    17040
ctcgtaaaaa tccataaaat tctttgtagt gaagaaaaga gcaggcctca ttaccccccaa    17100 gttgcccatg ttcccttttgt gctgtcccca tgcctttccc cacccctagc aaccaccctc    17160
aggtcctttt tgtcacctcc ctctggggtt tactccttcc agaaagttta tataaataga    17220
gccatgctgg gctggagaga tggctcagcc atcaaaggcg aggctcactc aaaattaaat    17280
agaatcttac agacttttttt tgtctggctt ctttaattag cataattatt ttgaaattga    17340
tgggtgttat gtcagtagtc ttgttttatt tctgagttgt agccggttat atgcttatgc    17400
catagttctt tggccagttc cttgtttcaa tatttggggg aggtttcaat ttgacatatt    17460
acaaatattc agttacaaaa cttcaaatgg tcatgtgctc atttatttcg ggtaaatgcc    17520
taagagtaga aaataaccca gtgttgcagg ctgtggtgag cttcttgaga taataccact    17580
tttccaaatt ggttgaataa ctgcattctt ggattcttga tatgcctcgc agccacccac    17640
ctcgtcagcc ctcaagggat cagtcccaag cttttcaaacc ttttagaatg tatgtgctag    17700
catttcttag tctttaattt gcatatctct aatgagcaat ggtgttgaat gttttttgttt    17760 atcacgctga tgaaccttct ccagtgagat gtctggtgca gtgtgctgcc cattttcaaa    17820
ttgtgaggac tctttatgtt ctggatatgt aagttataat acatatacct tgcaaatcat    17880
tgaatatcag tgaagtcctt tttgtcattt ttttctctt ggaaatgtgg ggttttcttttt   17940 tttgtgaagt tatctatgaa atcttatcct gtttttttaag tttctttcca aatctttttt    18000 ttttttttttg gtagttatat gctttataat ttatctgtta ttgggtatca tgacacacac    18060
ttgttatctc aacttcttat ttgggaagct ggggcaaacc cagctcacag cccaggctca    18120
aagacaactt tcatttagat ctgtggtctg ttttaagttg attttgtgta tgtaacacaa    18180
tatgggtcag agtttgtttc tctgtggatg tccttgatca gcattgcgct tgaagaagac    18240
tgttgtttgc agtgaagtgt ctttgtgccc tggcacacac tggttcacag atctggcctc    18300
gattctgtcc cactgatcag ttagtgcttg taccagtgac acattcctgc tattactgta    18360
```

```
attgtatatt aggtcttggt atcactgttt aacaaggtgg tggttatttt ggttttggtt    18420
cttaataaaa tagttgggcc tggtcgtaca catctttagt cccaacagca ggaggcagga    18480
agcagatctc tgagttcaag gtcagctggt ctatttactt tgtatattta agtcctaagt    18540
ggttttgcca atcactttgc aaacctttct tttaaaaggc caactggcag tttgtgattg    18600
cattgattcc cttcctatgt tgtgtagagg attttttggaa ctgatatttn cttttttttt    18660
tttttttggt ttttcgagac agggtttctc tgtatagtcc tggctgtcct ggaactcact    18720
ttgtagacca ggctggcctt gaactcagaa atctgcgtgc ctctgcctcc cgagtgctgg    18780
gattaaaggc atgcgccacc acacccggcg gaactgatat tttcataatg ctggtcttat    18840
tccatgaata gtataattct atatttattt agatctttta actaaaattc ttgattgtgg    18900
taaataacac aaagtttaaa gtttaaagtt taaagttacc atctcatcca ttttgtttct    18960 gttttttgttg ttgttgttgg attttgtttg ttttttgtttt tcaagacagc atttctctgt    19020
agtcttggct gccctggaac ccattctata gaccaggctg gcctcaaact tacagagatc    19080
ctctgccttc ccattgccag gattaaaggc acatgccatc actgcctgac tcatcataac    19140 cagttttttaa ctcatagttt aatattaacc acattcacag tgtgctctag aaccattgaa    19200
ctgccctgcc atctgcacga tgagttatct tttctggttc ttagtgtgac actctagatc    19260
ttgccttctc ctggtttgct tacttcgctc agtgccgtgc actcaagagt cacccatgtc    19320
atagtgtgaa caggatttct tgtcaacatt tttatttatt tatttatttt tggtttttcg    19380
agacagggtt tctctgtata gtcctggctg tccgggaact cactttgtag accagcctgg    19440
cctcagaact cagaaatctg cctgcctctg cctcccgagt gctgggatta aaggcgtgcg    19500
ccaccacacc cggctcttgt cacattgttt tccttcctac tccctcctgt cttctttcca    19560
acatagccag gactacaggt gtgcacaccg tgtctgccta ggagttcttt aaggctgagg    19620
aattctctat tgcatattta taatgctttt tttttttttgg tatccattgt caatggatgt    19680
ttgagttgtt ggacttctgc cacctggcta taaaggatag tgtgcttctg tgagtatggc    19740
tatgcacact tctcttttgaa atcctctttg caattaanta atttagtaaa tacactcaaa    19800
gtgggatcac tanatcatat gctcttttta attattttga gcagggtctt ggtttgcccc    19860
aaacttaatg tccttctgcc tcaatgtcct gagttgctgg gaatgcaggt tgtgccacca    19920
tggctaaccc cacctacctc agggaatgtt gctctcctta gtggttgtat catttttatgt    19980 accagaaaac aaagtatgag ggccacagtt tctttacatc accacttgtc atttcctctt    20040
tattttccta gagctgcgtc tctaacttgg caagccctgt agactgagct acatccagcc    20100
agtctttggt aggggtggtt ttgatggtgg ctatcctagc gtgagataag cttttgatatg    20160 tcccagagag aatctgccaa gagtttcttg catttgtaga ttccctgttc tttgctgctt    20220
gttcctttga tgcactttgt gggtggtgta gttgttttgtt ttgcttttgt tccttaatttt    20280 ctcttagcac cgttttttgta atttcgtgag acaagacat ttgggacagg atccctagac    20340
tatcttggtt ctgtaattca gtgggaagcc tcatagacca caggaaaatg atagtgttca    20400
ctattacagt tgattgcagt gaaagcatac agattattgc caggcgtggt ggcacattcc    20460
tttaatccca gcacttggga ggcagaggca ggtggatttc tgagttcgag gccagtctgg    20520
tctacagaat gagttccagg acagccaagt atacacaaag aaaccctatc ttgagaaacc    20580
aaaaaaaaaa aaaaaaaaat acagattatc attggtaata gaaaaaggca cttcaggcag    20640
gccagagggc acctgcttga gattccgtgc gatttatgca aacagtgctt aattctcctg    20700
gctacagcat gtgacaacac ccttgcagta ttttcaacca ggggaacaaa ctcaagcctc    20760
```

```
aatggccaag gtttttactg ttagcggtct atacaaacat ggttggcctt tgttttctac    20820
cccctttagg ggccaagcta actctgacct cctccgagat cacagtctag gttgctggtg    20880
tgtcccaagg catctgtaaa cagcccaata ggctactcca agggcttgca gacccctcct    20940
ggggtctgag cagcgcagaa gcttcttggc aggggccggg tctaggagac cctaagacac    21000
agagttcgta gctctactgc tcagtgggac cgtaaatctt tctaaccacc cggcttggct    21060
ttctgatgtc tttgcggtaa tgcccaaaag gaatcacatc ccaggtgttc ctttaccacc    21120
tgtttattct ctgcagagtg gtcccagact gtagtaattg tgcttatttg tgtcccttgc    21180
cccagagtac tcaggagtcc agaccttgtc tgtctcactt cactgctcag ttcctggctc    21240
ccagtgccct gtgttcaagt gactgaaatt cagctccgcc ccccccaac  tccccacctc    21300 ccaccaacac acactgtagc aaatgcagta atcagtactt agaaactgaa caagtttat    21360 gtaaccaggg aatggcaaaa gacacgaata tagtttaatt tttaagtttt ttttatatgt    21420
atgagaacag gcagttctga gctaccatga aagttctagg aactaagcct gtgtcctatg    21480
caagagccct aagtgttcag taaaaattaa aattacactg agaccttgta tctcacctac    21540
cagattggta agaaatccag gcattagctc ccatgattgt gaagttaaca gttttctaca    21600
ctggcaaaac tctaaactgg cgcaatctct cagaaatgaa ggcaggttgg caaatgtaat    21660
agaatttcaa atataccttg attcagcagt tattcctcag agaacttgct ctacaactgc    21720
attgggtaag tatatacgtg tcgctaagtg actaaggagg cctgccctgc agtgttgttt    21780
gtaaggcaaa aggttggaag caaattagat ttccactgtt agggatcagg caaataagca    21840
cagtgaattt ctacagtggc tgtgtgactg cctagaaagc taagaaatag aaacatgaag    21900
agacaggcac agggacacag gacctatagt cccagctcct tcagaggctg agacaggatt    21960
gggcataagt tcaggactaa cttggaggac agagtagcaa gcctgtctca gttgaaaaa    22020 agaaaaagaa gatgtctttg ttttggtgtg taagaacctt tgagtgcagg agcaaagcac    22080
agccttgtgt agcgggggcg gtgggttcca gctcgggtca gtagcaatca gaagttgggt    22140
tttacgagac agcagctcag gagcagggag accttaaacc ttcagaagaa aatgaggaac    22200
tgttgtacac ttttcatac tttctttctt taaaatcatt taacctttaa aataaagttg    22260
taccttttta aagttggaaa cacaaagaat aagtaagggg taagagaaag aggtagtgag    22320
tgtgagacct gtgtgagaga aaaccactcg ctgctaagga ggccaccgc  tcctagacca    22380 tttttgctt aggacagggc agggtggggt catgctctgt acaaaccaga atatccagtg    22440
taggagcgat ctattctggc ctaattaact gttcatacag acagatgcca gggctgtggc    22500
acccagaaag tcacacccat atttagttca tggtaaacat taattcatca tttagttaga    22560
attgtattgc taaacgcaga catcacagtt ttagctgttg acatgatctc ttccttctct    22620
gggaaaatag aagcctagtt tatttctggt gtgtgtgtgt gtgtgtgtgt gtgtgtgtgt    22680
gtgtgtgtgt atgggtgtgc tttagtcttt atgactttat attgctcaca ggataaagtc    22740
tcaagtcctt gatagggcaa ataaagtttt ttatacctgt ccctaaaagg accttttaa    22800 aagagcagag tttctagagc caggacccty ttctgtggga ctgcagttgg aggcaatgct    22860
ttacctctga gctacatacc cttttaaca ttttattctg agaccaggga ctagcacatt    22920
gtcttcaaac ttgtactttt tcctgcctca gctcctgaat tctgagaact gtaggtgtgc    22980
ccgccacacc cagctcagag tccagagctt actgatgtca ctattgctac tgcagagtgt    23040
ctgggataca gtagaagtct cctgactact tgtgggaccg tgccttaggt acttttctgt    23100
```

-continued

```
tgctgtgata aaacaccatg accaaggcaa attataggag ggctttattt gggttcattc    23160 ttacagggc  agcataaacg atcaccatca cccatcatgt cagggaagtt atggcagcag    23220
acaggcagag tggctgaagc aggaagtaat agagacagac agacagacat gcaaacacac    23280
acacacacac acacacagca ttgggaatgg agaggctttt gaaatcacaa agcctgcgac    23340
cacacctctt aaacctccca aatagcatca tcagttgagg actggatatg caaacattta    23400
agcctatggg gagcatttcc accccaaaa  atgggtctgc tgcaattgaa attaaaaaaa    23460
cccttacccc cctccgattc tcccaagctc ccatactgtt tgggaaatga taaattaagg    23520
aaaacatttt tctggaagca ggctgtcctg ggttcaaacc ctctgacatt cactagctat    23580
gtctatttct tcacctgtta agggatggca atagagtgaa aaatcaaagg atatgcacat    23640
gtcatagtcc ctgttttata gaaataattt tatgctgtta ctgaatgtgg agtgtattag    23700
tattgtgtgc gtgtgtgcgc acgcgctcat gtgtctggag gtccgaggac agcgttgtgg    23760
agtctttctc ctcccacctt tatatgggtt tcagagatga agctggggtt gtcagacttg    23820
gaccgatggg tggcaggcac cgttatttgc tgagccatgt gcccatggag tgtgctgcta    23880
atgagtggcg gtaagactcc acagtaatag tcacactctg tagttgaaag ctgggcagtg    23940
gtggcacacg cctttaatcc caacaattgg gaggcaaagg caggtgaatt tttgagtttg    24000
aggccagcct ggtctacaga gtgagttcta ggacagccag ggctatacag agaaaccctg    24060
ttttggaaaa ccaaaccaaa accaaaaaaa taagagagag agagattgat ttgaaggcag    24120
gttgtgtttt caatcacctt cctgaaagaa attagcttaa tcaggtactg tttaccaaca    24180
gtaactatta aacactggaa gttggctttc cttccatcat gtggtttcag ggaattgatt    24240
gttaggtttg ccaacaagtc cctttgccct ctgagccgtc tcaccagctc tgttactgtt    24300 cttttttattc attttaccat tgggnaaatt tgttttaaca aatgaattta aaaataccaa    24360
aataaattta aaaatgaga  aaaagccagg ggccaatgag atggatcatt ggataaggtc    24420
acatgccttc acatatcatc atatgtaccc aagtatctgt acacacacac acacacacac    24480
acacaccacc accaccacca ccaccaccac caccaccacc acccccaca  catacactta    24540 aaaacacagt aaagccggga attgagacct agtttggtaa tggaaaagct cttgctgagc    24600
atgtatggag ctctggggtc agtttttagc acggggacag gaagctaagc acagcaaaaa    24660
tgagcataac agctcctgtg tgagctgctg aaacacgtga cggggtcagc cctgcaaagc    24720
caaagctgca ggacttcatg acacagggcg acaacaggat gtttaagagg actcccagtg    24780
agcgtccagt gttgatagtg tagcagaagc cagaggcctc gagccagaca aagaccgtgc    24840
aatgaacatt tgcaagtgaa gctgttgggg caaagggta  tatatactgt gggacactcc    24900
acagcgtccc tgggagagtc tttgtttat  tttcttttgc aggagttagg gtccctctgg    24960
gtagttctgg ctggcctgga actcactaca aacaggctga cattaaactc ccaaatgtca    25020
ggattaaaga tgtggctacc atgcctggct gggagatttt tttttttttt aactaagcaa    25080
ttttaaaaag tgattgtagt cttaaaacaa tttatttatt ttatgcatat gaataccatg    25140
tagctgtctt cagacacatc agaagagggc atcagatccc attacagatg gttgtgagca    25200
accatgtggt tgctgggaac tgagctcagg agagcagtca gtgcttttaa ccactgagcc    25260
atctctccag ccccataatt gtagtcttac atggtgttgt gagaaagaat atggagagat    25320
atcttgaaca ccactatatg cttttttaaag tactattaat aatgagtccc agcactcggg    25380
aggcagaggc aggtagatct ggagttcga  ggccagcctg gtctacagaa tgagactata    25440
gccaggacag cttggaatac atgagaaacc ttgtctggga aaattaaaat aacaacaaca    25500
```

-continued

```
atactaaaat caggtaggga gtacttcatg aatttgaaaa gatgagatta ctaagtttgt    25560
agctgcatga agaacatttg gaggcggaaa gttggctctg tggtggttaa gagcacttgc    25620
tcttccagag gacccaagtt caattcccaa ttcctacatg gcagcttaca accatcttta    25680
actccagttc cagggatca tctgatgccc tcttctggcc tctgtagaca taggtgtatg    25740
tgtggtgcat agaaatgtat ggaggaaaaa cacctataca caaataaag aaatcataaa    25800 gaagaagtgt tggtacaagt atatagtatt taagccaagc ctccaaaggg gggaatggtt    25860
gcctgaggag gagaatagaa ggaggggtga agtgagccag gacccaggta agcgggaggg    25920
agggcctggc ttcctcgggg acagcagtaa ataataatcc agacattagc actgtctgta    25980
aggagtcctg tggagccgt taccacacat cccaggtgta tgtcttccag gatgccttgt    26040
gctgagagtc cggcttactg aatgcatttc tcgttcttta gaatgacagc caagaacggc    26100
agcagcagca tgacaggcag agacttgaca accctgagcc aatatctaat gggcggcccc    26160
agagtaactc aagacaggtg gtggaacaag atgaggagga agacgaagag ctgacattga    26220
aatatggagc caagcatgtc atcatgctct ttgtccccgt gaccctctgc atggtcgtcg    26280
tcgtggccac catcaaatca gtcagcttct atacccggaa ggacggtcag ctgtatgtat    26340
aagtgcttcg ttctctgggc tggtgtggct tttttcctcgt agcttgttgt tatcctctca    26400
aagatctgtg gaccatcttc catctttcct gatggccaga ggcagtgggg atgatggcag    26460
tgatgatgtg atgtcttggt tttgttgttg ttgttgttt agttctaacc ttttgaattc    26520
ttacttgtga gccagcagac atggtagcag ggcctgaaat cctagcactt agcaaatggc    26580
tcatggaagt ttagaggttt aggaaccatg gctttggggg accaccatgt ggtgattgag    26640
acacaagcat gatggcatat gcctaatcac ttggcagtga gacgggtcag tcaggaactc    26700
aagtccatct tgtgctgatg cagattccag gccaggctga gcgacacagc aaagcaacca    26760
cattcctatg gtccctatct tggcttgtgt gttaagtctt taaaaacaac tgccttcatc    26820
tactgggagt agatcctagt atttctcata acagcctgtt ttcactgttt ctcaggctag    26880
tctggaatcc actgtgtagt cttggctagt ctcaacttc tgatcctgcc tcagcctcct    26940
gagtgtgagg attacaggtg tgtgccacca taccctgttt tacgagactg ttatagaaac    27000
tcaaatgaca ttctctttct cccacagagc agtgcagggg taggcagtcc agattggtat    27060
ccgggtcttt tattcaacaa agcatgtgtg ctcctctctt cagcttaggt cctagatttc    27120
cttagggtcc agactagagc ctcagttttc atttgacagc aggagggagt tgagaagggg    27180
acataggcat catgtagccg agagcactcc ctgcaggaac tacctctata gcttgttcag    27240
agttccttgg tcactatgca gtctcatggc cacacctgct gtaagggcag aagtaaggtc    27300
attgtgctgg aagccttggc acttggaatt aaggcatttt tatgtggggc tgtcgagatg    27360
gctcagcagt taagagcact gactgctcct ctagaggtcc tgagttcaat cccagcaac    27420 cacatggtgg ctcacatcct tctgtaatgg gatctgatgc actcttctgg tgtgtctgaa    27480
gacagctaca gtgtactcat ataataaaa taaatatttt taaaaaaggt attttttatgt    27540 aaatgaaata cgagaagaca actccaataa tggtcaccct agagataaaa aaccattgct    27600
taaaccctgt gacctctctc taataactgt tgtccagcct tagtagttac tgtggcagca    27660
tctggttatt taacagagtc tattaagcta tggagaaaac cttgggtgag atcattattt    27720
cagaacaaag catccactag atggagccag tgcctacctg tgagttcatc tcttcatagt    27780
ctatttcctc ttactcagaa gacgttattt tagaggatag ctatttttct taagctaaaa    27840
```

```
actattgggt acaggggttgg agaaatggtt tagcagttaa gagggtgcac cactcttgtg   27900
gatgtactga ggggtccata acacccacgt cagagagctc ataaccagct tcagggattg   27960
ggtgcctctg cccttcatga acatctgccc acattcacgc aatgcacaca cacacaattt   28020
aaaataaaaa tatatgccta catttaaaaa tattatttga gtgctgcttc acccctcctc   28080
cctctcttta gccctcacct ttcttactct ctagccctcc ttctctctct cccttccccct  28140 ctctctccac atggccatgg ccggcctctc tctctctttc taccttctct cttttcccctg  28200 catttctaca caaagctct aaaaccattt aaaaaaaaat attacctaga gctagggtgg    28260
tacagaccac aatctccaca cttggaattc aaaggcagga agatcacgtg ttcaagtaca   28320
gcctgggcta catggtgagt tccaagctag cttggggttt cttattagat tctgtgtcaa   28380 aaactaaccca accaaataaa aatatccttg gttgactgat gacctgcaaa aggcaccttc  28440
taaaagactc attaaaccgc agacctcaca gtgaattaca gttttaagag ttgtgctgtt   28500
tgacatatgc attaacactc tggtgttttg tttccctctg tagaatctac accccattca   28560
cagaagacac tgagactgta ggccaaagag ccctgcactc gatcctgaat gcggccatca   28620
tgatcagtgt cattgtcatt atgaccatcc tcctggtggt cctgtataaa tacaggtgct   28680
acaaggtgag cacgaggcag tctgctgtcc gccttgacct gcctatgggt tgtccttgtg   28740
tgtgtgggag gggaagggtg ggagagttgg gggcggggga gatgtgtatg caggcctgtg   28800
catgtcagag tgtgcgtgtg cagttggtan gaccactttg tggaatgcat cttttccttc   28860
catctttgct tgggttttgg atatcaaatc tccaagcttg taagcgtcac gttctgagcc   28920
ccttcacagc ctccttgtct tgacttggtc taacaaagag gaagtgtctt atattttgga   28980
tctaagttat ttttccttt attctgaagc atgttgaaag taccagaaga catacatgga   29040
aaacaggtgt tttcatgtaa ggtcacatgt tttcagtatt ttgatttata gtgtgcctat   29100
ggcattccaa agacttttgt atatattgtc cttaacaaat agtgctatag aatttaagtg   29160
ccccataagc caccttcaga tgctgctact gaacgcagta gtgactggcc cctcacttga   29220
gaaccagcat catttgctta gtctctcaga gcagccctgc ttcttacctt ggtcaatggg   29280
cacagggaga agttgcagca gagatgcagg cccagcctgt cccctctctc cctctcctcc   29340
cctctcttct ccctctcttc tcccccctcc ttccccctcc tctccctc cctccctccc     29400 tccctccctc cctcagtaag caactgcgtc ctggacctca gccacccagc acatgcttca   29460
tactcaaacc tcagaaaatc aacaaatcaa tactggtcat ggaatcttca ggtcgtcctc   29520
agtagtagga acagtaaatg ttaactctcc gtattgaagt ttactctctg tctacattat   29580
tttctcctag atttttcttt ggggtttgtt ttgttttgtt ttgttttgtt ttttgagaca   29640
gggtttctct gtgtagccct ggctggcctc aaactcactc tgtagaccag gctggtctca   29700
aactcaaaag attcacctgc ctctgcctcc ccagcgttga gattaaagat ctgcgccgcc   29760
accacctgac aaatagcgtg ttgtgcagcg gttttctccg cacgtctcac tgcacctgtg   29820
tctgtctgct tgccatccct ccctccctcc ctccctcagt aagcaactgc gtcctggacc   29880
tcagccaccc agcacatgct tcatactcaa acctcagaaa atcaacaaat caatactggt   29940
catggaatct tcaggtcgtc ctcagtagta ggaacagtaa atgttaactc tccgtattga   30000
agtttactct ctgtctacat tattttctcc tagatttttc tttggggttt gttttgtttt   30060
gttttgtttt gttttttgag acagggtttc tctgtgtagc cctggctggc ctcaaactc   30120 actctgtaga ccaggctggt ctcaaactca aaagattcac ctgcctctgg cctccccagc   30180
gttgagatta aagatctgcg ccgccaccac ctgacaaata gcgtgttgtg cagcggtttt   30240
```

```
ctccgcacgt ctcactgcac ctgtgtctgt ctgcttgcca gtctttacct cctggtccct   30300
ttcttggcct tagtggacac atcctggacc tcagctgatt agggaccagg cttgttcttt   30360
tgcctccttt tacgatttta ttgggggtag aattcgcgtt cagaatttgg ccttgattga   30420
ctgacaggca ttatgtaaaa ttcctctcaa acctagtcct tctttcctaa aggccatggt   30480
ccttggcgcc cccatggaat ctgtttatct gcttggcaat acttccctag ttctatccgc   30540
tgcctttgca aacttggttt ttctggatcc tctcgccatt ggcttgttag tgtgcgttct   30600
gaccttggtt cctttcctcc tctgcagttc ccctcaggct cacaacccag tcccagactc   30660
tggaggcttt ccctcctttt gtttctcaaa agccctgat tagggctgga gaatggtttt    30720
atccgtagga gcactggctg ctcttgcaaa ggacatgaaa ccgatgaatt tagtttccta   30780
ctcccacgtc ttggctcata ttcgttcctc actctgtttc cagggatcc aacaacaacc    30840 tcttttggct cctggggtgg caggcacaaa tggcacttac tgcatacata tacacacatg   30900
cacagggaaa ccatgcatac ataaggaa aaaaaaaac ctttgaaaca aaatcactta      30960
ctctctggat taattttgta ccctcaaatc taaccttaaa ttttttttaaa attaagttta  31020 tatagtgtat gtcatgtgga catgtatgtt ccatgcttca tatgtaaaat tcaaaggtga   31080
ttttgcagga ttcatttctc tccttccatg ttgtgtgaca aactttccct gcagcacaca   31140
tctgctcgcc aaaaaaaatg agcgtaccac tcagtagcaa attaaaaaca actgacccgg   31200
ggtctgacaa gcgagccagt gaggcaaagg acaaactttt tcctttcctt ttttccttt    31260 tggaaacagg gtttctctgt gtaccctgg ctgtcctcga actcactctg taaaccaggc    31320
tggcctcaaa ctcaaaaatc tgcctgcctc tgcctcctga gtgctgaaat taaaggcgtg   31380
cgctaacact gtctggcaag gatatactta cactgaaagg ttgcttacaa ggagcaggga   31440
tgattcaaaa gcagctctgt ccctgagagg ccactccaaa aaaaaaaaaa aaaagctgcc   31500
accctggagc tccctgcatg gctgtgggca gctcccagct acctttctgc atttgggctg   31560
ctagaatctc caccccaagc ggtcgtttgc tcctttgtat gttgttgccg actgggccgc   31620
aggaatcttg tgaggttctg ttccctcagc tatgtggcct ttgatttcgt ttgaggcttc   31680
taaagggaat gtctcagatc agaggaaaat aaatgtcatc caagaggacc tgcctcagtt   31740
gtcacgcctg ccagcaagtg ccttcaccaa caaagctatc ttgctgtcct gaagacaact   31800
ttgattcagt gctttcagcc taaaagtcat tgcttattgg acccatggtt tgttggttga   31860
tttattaatt ctactttgat atctacaaac acatatcctc catcccctta tcttcaatag   31920
tctgctttgc taactttttt ttaaacttta tttacttatt tatttaattc attttacagt   31980
ctaattgctg ccctccctc acacagtccc cttccccctt ctcctctgag agggtggagg    32040
cccccattgg gtctcccccc accctatcac atcacgtctt tgaggtctag gtgcaacctc   32100
tcccactgag gccagacagt gcagcccagt gaagggaaca tatttcacag ataggcaaca   32160
gctttgggga catctcctgc tccagttttt ggggtaccca catgaagacc aagctgcaca   32220
tctgctgcct gggtgcaggg gcctgctttg ctggctttga tgttgctcct gttcatccat   32280
tgtcttcttt cttactggtc acttcctttc ccaagttcct ctaggccagt catccccagg   32340
ctagcctttc tacttcttta gcttgatttc acgtgccaca aaaacaaagg taccccagtg   32400
tcttggggct tttttaattg ttgtttgttt tgagatagaa cctcattgca tattctggct   32460
gtcctagagg tcaatgtgta gaccaagcta gcctcagaat catggattaa aggcaataat   32520
cagccatgcc ttgtcctttt aatgaaagtg gtaatggtcc ctcccatcac cctctttccg   32580
```

```
taattaaggt atattttcaa attccttgca ttttttacgg tttgttaata ctgttaattg  32640
aaatttagta gttatagttt tcatttctag aatttatatt tgtttgtttt aaagatggta  32700
gatcattttg gggataattt ttttgtccag atttaatttt tttcctatta gtttcctgtt  32760
tttatgatat cttaagtttt ggggaaggat aattctattg acttttactc atggtgattt  32820
ataccgtgaa tgagtgattt ctggtcattt tgagtttata tctttgaaga gtttattaga  32880
gtcattttgc atgcacgtga gcagttgaag attggcacat gccaaaaact gcctttgacc  32940
ctcatgccac ctgacctgat ttctattttc ctttaaaatt tttttttttt tttagggaaa  33000
agagggcttc taaaaatttt tccttttctt tgtcacttct aactgtattt gagattgtat  33060
tcaactatta agattattgt cttctaaaaa ggaacagggc ggccatttca aaataaaaca  33120
ttcctatgag gggggattga ggatgatcat aggaaaaata aaaaaaatat atgcaaggga  33180
caggtatggg agggctgcag gtcaatacca caccagcatc aattgtattt ctcataccct  33240
tcttatacta cagtaccgag ggaagcaaac ccataggcta acaaaaacaa ttgctgaaaa  33300
atacacaggt gacatctatt ctcatccaaa accctccctg ttccttccac caaggtcaat  33360
aaaatcttca ccccttgcc ttgagcctca attgcacctc ctcttattgt tccatgcctc  33420
agcaggccag gaaatctgcc atcagaccct cacctgcctt gattctgcct ggcaggcaga  33480
ctcacaaaca cacacacaca ctcactctct ctctctctct ctctctctct ctctctctct  33540
ctcccccctc tccctctctc ctctgcttcc aacatagaaa attttagaga atctgtccac  33600 tgtatttta taaatacaga gagatgggtt cattttagtt cagcgttttc agggttagca  33660
aaaataatgt ctattgttgt gggctacagg gtatttctca gtggtacttg catgcattct  33720
tagctgccct cacctaacag gcacacacac acagccctat cctggccaga gtggggtctc  33780
agcgcctccc atctttgtct tttctacagc tgctatgccc ctcaaatcct gggttgtctt  33840
cctactttgg caccaactgt tgttttgacc ttctgtctca ccgtggtta gagtgcacat  33900 gtgaatggga tgtgtgtgtt gggatgcagt gttgtttttt gtttgtttgt tgtttgggt  33960 ttttttaaata tattttgtt ttgttttcaa gttaatgctg aactcataga atgggttggg  34020
aagtgatgta ccctcctggt ctcttttctt catttacacc taagaattgg aacatatgtg  34080
ttgtcttgct gttcgtgttt attgagtctt ctttcacata aacaggtttt tctagtattt  34140
atatattgta taatttgggt tatatcttgg gcactttgtt ttcagttttt aaaaatcaag  34200 tatttttattt attactagtt tctgtcaaga gttcaggcca ggaaatttca tagtgaaact  34260
ctatttagaa aacaagagtc tggagagatg gtcagcagtt aagagcactg gctgcttttt  34320
cagagtcatg agttcaattc ccagtactca catggaggct cacaaccatc tgtaactaca  34380
gtttaggaaa atttgacacc ntcttctggc ctctgccctt gactgactaa caaacacaca  34440
tacacacaca gtgcataaat atacatgtag acaaaacacc catacacata aaatacctt  34500 ttaaaataga acaagagtca cggccacata cgcttcctgg gagatagagc agtgaactcg  34560
aatggcttcc agataggatt tctggttctt tgggactttt ctgtcttgt tcttccagct  34620 agacactgag actgtttcct ggtgtcaggg ccaaaagctg ggaagtcagg gagctacaca  34680
agactcgtct cataccctga tgaacaccgg ctcccgtcag aatgaagatt ttgttctccc  34740
taagtgcagg gctccagcct cctctttcct acgacttggg ggtggctggt ggctggctta  34800
agagagacca gtggatctcc ccttgtcttg ctagtgccag ctctggcagg ccttgcatgg  34860
aagtgagcag aaaggaaggg ttaaaggcta ctgaagccac gccacttgca ctttcctagc  34920
tccctgcctt ctctcgtagt ccgcagctag ctgaggtttg agttcttcca ggtgcagctg  34980
```

```
taaacagaga agagaccgta gaacgtgctt aattctgtca gctagacctg gccttcacat    35040
ttgggtcagt tctgtacatg ttttaattat gctaaatttg aaaacatctg gaatgttggt    35100
acccaactct atttctaccc tcgttcatct gtgctgtttc gtgttgtttt ttaatgagtc    35160
ttaggaagca cagccaattc catacaagaa tgttgtttac tttgacttcc agcatgaagt    35220
aaagcgagct tttgagccag acattcaaaa gcagcttgct gggacctgtt tgcaagcaag    35280
ccctgagggt ttctcccagc agtgtttgat tgtacagtgt ctgcaggaag ggcgtggggg    35340
ccctgacagg gacagacaca gaagagccag ttggttgtga tgcgtttgtg acagatgatc    35400
tgtaacttta aaggcatgag gtttctagca cggatggctc aggtttaaag agtgctcagt    35460
gctggcagca gagctcctga ctctggcctt tggggagccg tgggagctgc taagctggag    35520
acttgagaag gcttgcttgc tgttgattgt ccagactagg ggtgctcctt aaggctttga    35580
caatcatagc tgaccagtct gaactggaaa gttttacatc cttattacag gcaaattaca    35640
atataaagaa tgaaacaaca tggtaagtca gaatgtccag tgcccataga gaccagactc    35700
tcctgagaac tgttcagtgg gggttcgaaa gaacagcata tgctcttaac tactgagccc    35760 tcgtttttt ctaacagtaa agacttttcc tacttttta ttttgacatc atgatagttc     35820
cnaaaattta aagtagaaga tagctgttct attaaagcct acacacacac acacacacac    35880
acacacacac acacacacac acacacacaa acacacatat atataaatta tacagaaatt    35940 atttttaaaag cctgtcatat aacagattca tttggtgcta cccaaaactt acgatacaaa    36000
taaacaacta caaagggaac catcactaaa ctaagacaca caggacctat gcttcatttc    36060
agggggaacc ccaaataacc tttatcatgt tagaggagcc atgtccattt gccatgtttt    36120
gattacatac atctctccaa acccttatt gctctttttg tccatatttt tttctttcta     36180
tttatgggcc agagtaaata ataaaaatta tctttattga taactgtttt ttgacaagtg    36240
aatgccaaat gatgtctttt gtttatttt aaaaagaact tgggactggt gagagctcag     36300
caggtaagag cactgactgc ttttccaaag gtcccgagta tgtgtatatg tctttctgtt    36360
tcattctctg agtgcaccca ggattctcac ataagtatgt gctgatcccc aaagctgcat    36420
ttgttctgac atttaaaagg agaacatgga agccaggcag tggtgctgct cacctttaat    36480
cccagcgctc agtaggcaga ggtaggcgga tttctgagtt caaggccagc ctggtctaca    36540
gagtgagttc caaatcagcc aaagctaccc agagaaaccc tgtctcagaa aaagaaaaag    36600
tagacgatgg acatgggcta gaaccagtaa tgtagcagtt gccagcgtgt gaaaggctgg    36660
tgtaccccag cctcgacgaa ggacaactag aaagcagact gtagcacata ctgtttctca    36720
tgttaaaagt ctccttgttt ctaaactgtg ggatctgttg gttacatttg agttgtctct    36780
cttctaggtc atccacgcct ggcttattat ttcatctctg ttgttgctgt tctttttttc    36840
gttcatttac ttagggtaag taatacaggg ttttggtctc tctctccatt aactctgaca    36900
tccaccactc ccttagagcc atgtaccttg ctgatgaatt agtctaagta atcatttttt    36960
ctacatactg tatcttaaca ggtacataaa agatgagtta gtgttggtga tggggaccat    37020
gtgccacagt atgcatgtgg cagtcagagg ctaagtggtg gctgtcagca gggttttccc    37080
tagagagaag tatgggggag gggagaggag acttgttacg agtctttatg taaatgtata    37140
cgtacctagc taagagttga ggttagtttc attttagaat acctgaaatt cttagtataa    37200
tatacattgc aacctcattc agaaacttca acactttgc tttatttag aattttaaaa      37260 aaggagaaaa accatcttcc tagacagccc catgtcccac agtttgtgct tgagtatatt    37320
```

```
ctctctccttt tgctacttag ggtgtctact atagttacaa tcttgtagat gatagagttt    37380
gtgctccaga aggtaaaaca gttttcttta tatagaaagt taaccagggt ctgaggagat    37440
gactaagatg acagtgtttg ctgacctgaa gtcacccatg aagacctgag tttggatgct    37500
cagaacctac atagaagcag accagtgcag ggacaatttc ctgtaactct agcaatggga    37560
gtcagtgaca gatagatccc agggacttgc tggccagcca agctagccaa acagcaagc    37620 atcaagtttt gtgtcaaaac ataaggtga atgtcaactt ctggcttgta catgtgctct    37680
tacaggcaca ctcacccaca gagagcacac atggtgccag gcagcgggct agcagcagca    37740
gatccatgct ggagagcatg ctcagtgcac acgaggcctt gaggtccatc ccagcttcac    37800
acagacaagt ctagtcatcc ttctagagag tgataaatct cctgctgtat cttagacac    37860 tgttctcatc agtgtctgat gatgttatat atagtattat aatgttatta tgaaataata    37920
ttgtttatgt tctcactatt catttttttt ctaatttcag acctttaaag tagaatttca    37980
taaaatacag tatgatagtg taggggatat gatttttcttt ttgtagtttt tgttttatt    38040 tttacaggtg tgacctgtga taatatgtgc tcatttatgt gaataatgta atacctgtta    38100
gaataagttc tgctggagga aatgtgtta tttaagagca aggtgctaca taaataacag    38160
cacagcatag gtcataggaa aagcaaatat ggaatgtgaa tagttaatat ttcagaatct    38220
tcgctctaaa caatgtgttc atgagagtta ttgcacataa gtcacttcaa atccttgcgt    38280
gattgttttc agggaagtat ttaagaccta caatgtcgcc gtggactacg ttacagtagc    38340
actcctaatc tggaattttg gtgtggtcgg gatgattgcc atccactgga aaggccccct    38400
tcgactgcag caggcgtatc tcattatgat cagtgccctc atggccctgg tatttatcaa    38460
gtacctcccc gaatggaccg catggctcat cttggctgtg atttcagtat atggtaaagc    38520
tcaagactga cactttgtcc atcacagact cactcactgg tgtgctttcc ttcctcttct    38580
agtcctcttg atttaaggaa actcttaatg cttatctccc gtaggctcca gtggttttcc    38640
tgttacactg ctaaggattg caaggcaagt gctgtggcct gagccccagc gcagcctgag    38700
agtgagagtt tgtagttcct tgggactctg agctgggttg atgggaggag gccctgctca    38760
gaaggcttag gttcagaact cttctaccca tatgtgaggg gctggctta gtccccagac    38820 cccaggaaac aaagcagcaa agccaccagc cgccaccagc agttcccctg aattttgtaa    38880
gttgggaaca agtctccagg cttgtaagtg ttcagcgaga cggtggatac tgagatgtgc    38940
tagcagcagg ctcacactgt aaactgttca gctcatgttt gaaactgtat tctattttgg    39000
gggaagggct tgtgtcctga ctgagtgtag aggtcagagg actgcttcag cagtgagtgc    39060 tccctccct caggggtcc tggggaccaa gtgaacggag aagggcaggc atggtggccc    39120
gcatggctac tgagctgtct cactgccctc agttaatctt ctccctccag agtcttactt    39180
tatttatgtg tagtgcattt tgcctgtaag tgtgtctgtg cactgcctgc atttccttgt    39240
gcctgcagag gccagagaag gggctcatat cttctcaatt cattttaag atcagaatca    39300 tatagcaacg tgagtgcaat caccccttta aagattaacc tcatcctgac gtgtgtgtac    39360
atgtgcgact cagcaccggg aggtagaggc aggaggacca gagtttcagg gttatctatg    39420
actgatgtag taagtttcag accagcctag gccactttaa acccttttttg aaaaaaaaaa    39480 tgttttttaa ctaaataagt agtaaactat taagggtagt aatgtcctcc tgtaatccca    39540
gcacttggga ttcagctgaa aggcagaaga attagaagtt cagtccaggc tatgttttga    39600
gagcctctct ggagagaaaa gcagttctga gagtgaggtt tacatttgta aaagaattcc    39660
agtgcctgtt tgtttattgc atttaaattc tacagaaaga cctgtgtgta gactccataa    39720
```

-continued

```
gtgttgtgaa ggtcctcagt aaaatcctat tattttagct gggcaatggt ggctggtgca   39780 caccttaat cccagcactt ggaaagcaga ggcaggtgga tatccatgat ttacagagca   39840
agttccaggc ctgccagggc tacacagaga aactgtctgg aataaaacca aaacaacaa    39900 caataaaat aaatttaaaa aaatttaaac atacttttta acagctgctg tcctgaaaag    39960
tcacaataat actctagcca tggtaacggg gcctggcttt atcctccagc tgttgcgcca   40020
catgaaagcc aaaaggagt ctgttgtcag ggacgagtca gtggccactg ttttacagag    40080
catctcctta cactgaggcg cgtggtgact ggaactggaa actcgtcccc cttgagctga   40140
tggagcaaag cctgtggcgc tagaaccggg ccagttctgt tgtccacttg agcaactgct   40200
taaagtcagg ggttagaaaa gtcacctcaa cgctcacttc atggcaaact tcattcttgg   40260
tgttttgtca gtcgctgaga gtaggagtac cattgtaagc tagagagact cagccagaaa   40320
aggacttatc accaagcctg acaacctgac aagcccagga gtcacaaggc aataggagag   40380
aaccaattcc tgcaagtttc gtgtacacac acccttgtgc aggcaggcac aataaataat   40440
ataatttaca atcccgcccc gggagtcggc aaggtagtta tcatagggct tttgttgcta   40500
agaagcttga aggttacaga ggtaaattat ttgcctggtc gcttgcatgt ggcttgacct   40560
aagagtctga attcactcca tgagttactc tctccacgac cttcagcctc tgctcacagc   40620
acaggggaga ccccgcagct tcaggtcttc tgagtgtgga cgtgctgggc acccagtgtt   40680
gacatagtga ctctcaacct gttccttaca aggtctcaaa atggtctatc agaagtgttc   40740
tgaagccttt tacgtaaatt aattttcatt cattttaatt gtgctaaaaa taactgaatc   40800
tattcatttc aagattctat aaggggaaac atgtcataaa accaaaatag gtacaggatg   40860
tggcagcttt aaaacagctg aagatctcat tagttgcaag cacaggaaag cttgcttttc   40920
tcacttgaac atgtaaatgg aagtgtagag gagtgttacc actgtgctgt ttttacgttc   40980
tgcggggagt gactgaaggc ctgaaggaag tgacgtcagc tgtcaagtct cccattcctg   41040
ttttacctat acctgtttga tatttttaaa tgtttgaggt tttctgcatt tctgtaacat   41100
agaaaatgaa agacaaactg tagtttatgg ggggaaatgg tgttagaacc agacataatt   41160
taggcctatc agggcttctc tcagatcagt ttttatcacc accagatgtt ctgagaccta   41220
aatatttgtg aaataccttaa atgactagaa actgaagaaa tattaaatttt tgtcatatac   41280 agagctatca ttttatttaa gtgtgttgct ctattatggc aaattccttc gttatgtcta   41340
cttgctttgt agtgctaggg attgagtgca ggtctcaggc tgttcaagt aagtgccgaa    41400 gtagctcacc cctcctgctg tctgtaaagc aggacactct ccagccagag cagcacacac   41460
acaccctcct gctgtctgta aagcaggaca ctctccagcc agagcagcac atacaccc     41520 tcctgctgtc tgtaaagcag gacactcact cctccactct gctcttggta ctacgaaaag   41580
ttgaatattt ggaatggtgt ctatttgtaa tttataggtg aatttaaaaa acaaaaaacc   41640
tccctgccat ttctgcttgt tccacaatga gaactattct agaatagttc tgtcttgctg   41700
tctctgcctc tttccttcag gctaagaaga aacatgtcta gacctcagta atcacacact   41760
gtagattgag cacacagtgg tacggccaga gtataattta cacaggtctt ctatgggttc   41820
tgttttattt tgtttaggtt gcttttctc tggctgctaa aactgcaaat attttcatat    41880
ttacccnaca cttaaaaaaa aaaattagac ttgtttcttc aggtaagtcc tcccctgcgt   41940
atatccactt acacaatcta gtcagtatac tttattgggg tctttttta tttttctctt    42000 tctagatttg gtggctgttt tatgtcccaa aggcccactt cgtatgctgg ttgaaacagc   42060
```

```
tcaggaaaga aatgagactc tctttccagc tcttatctat tcctgtaagt atgctggagc   42120
aatgctgtgt tagtgcattc agtgttaagg tgcccgtgga ggtcagaagt cagaagagag   42180
ccttggatcc ctggaactgg atttatagat ggttctgagt caccatatgg gtgctgggac   42240
tcaaacccaa gtcctctgcg agagcagcca ctgcattcat ggctcaaccc gtaagccatc   42300
tcgccagccc cagtacattg ttttatgttt gtttcttaac ctgcaatctt gtatggtttt   42360
agtcctgagt tacttctgca cagagaccat tgttttctgt agagaagtga gcctcttgct   42420
tgctagagca gtgtcctggg tttaggaact cacctgcaac tttgtctttc tcaacagcaa   42480
caatggtgtg gttggtgaat atggctgaag gagacccaga agcccaaagg agggtaccca   42540
agaaccccaa gtataacaca caagtgagg tggagcttgt ttataaatgc cctagttttg    42600
caggtccatt gtcatttgta gataaataat tgaaatgatg aaggagtaat tttaaccttc   42660
gaagtctttg gtcacactct ccttgctgac gctcagggcc agagcacttg tctgagaagc   42720
cctggatgta gggagaatcg tgataaggaa agatatcacg agagtctcct agagaaacag   42780
gctctcccta gtaagtacac gtaggactat tcacggagct gaaatccccc cacacacaca   42840
cacactgtga gttcaagact aaccctgact gtgtgggag atcttgtcac agaaagggt     42900 gggagtgcaa gggtctcttg tccagtatgt ccaaaataac tgaaaacatt aggtgggagt   42960
gcagtcaagg ttacactagg aaggtcagta ntatttcagt ggcctgggta atggtgacaa   43020
ccaaggactg tgatactgca gaaggcacta aagaaaacat cagaagctct gtcagaaaga   43080
agtgaagaac agggtggtgt aaaactgaag cagaaaggag ctttcttaaa aagacaacct   43140
tagaaagttg aaaagaaaa gtaagatgtt aggcctaatt aaggctatag gcctaattta   43200
aagtaaaata aattttatct tatatgcata catatgtgta tgtatatgta tgtgtgtgag   43260
tgtttggcct acatgtatgt agtgcacata catggctggt acctgtggag gtcagcaaag   43320
gacatccgat gccctgggct tggtgctag tgagccacca tgtggacact gggaacaaac    43380
cccaagtctg ttggaagaag ccctctccag ccccacgtgt catattgagc taaagagaaa   43440
agtcgtgact gtctgcctta atcagggtca ctattgggt gaaaccaaac catcatggct    43500
aaagaacctt gggaagaaag gggtttgttc agcttacact tccacatcac tgttggtcag   43560
caaaggaact caggacagga actcaaatag gacagggacc tggggcagcg gagggcgctg   43620
cttactggct tactccccat ggctgtctca gcctgctttc tttctcttga acttgtacca   43680
ccagcccatg gatgtcccac ccagaattgg ctgggctttc ccccatcgat tactctttaa   43740
gagtatgccc tatagggctg ccttcagctc cagctctatt gtgtggaggc attttctcaa   43800
tggagggtcc ctcctccgtg atgactctag cttgtgtcag gttggtgtgg tagccagcac   43860
attatttctt gtgtattttt ggtgagttaa caaatgctga ctgattccct aggagtgtgc   43920
tcaatgtttt cctaggctct ggggagagag gactgaacaa gatgcttcct gttggtgttc   43980
acaagggtgc aggttcttca cgattcctgc tcgccacctt tgacatactg ggttgtcggc   44040
tgccctcatt tccctgtggt cctgacagtc acagtgctgg gcatagccag accgcatgca   44100
gggaacatgg aagccatttc ttccttcctt aaaaagagga aataaggag aaaatgtcag    44160 ccctcctaga cattgccaca tcatagttcc tccactggag aacttacatg gagaaaagga   44220
attcctgtgc ttgccttaac tgatactccg ccctctggaa cgtggcggcg atggtctaag   44280
gattaagtgc tctgattaac cttctctctt aaggagcgg agagagagac acaggacagt    44340
ggttctggga acgatgatgg tggcttcagt gaggagtggg aggcccaaag agacagtcac   44400
ctggggcctc atcgctccac tcccgagtca agagctgctg tccaggaact ttctgggagc   44460
```

```
attctaacga gtgaagaccc ggaggaaagt acgtgcatca cctctgcctg acatcacggc    44520
ggtgacatca cggcggtctg tcagtggcag ggttatctgt ctttcagagg atgttgagtt    44580
tttctgggga aatagcttat tcaggtgttt gccacacaaa cataagaggc tgagtttaat    44640
ctccaccact gtgtgtgtgt gtgtgtgtgt gtgtgtgtgt gtgtgtgtga gtgtgtgtgt    44700
gtgtgtgtgt gtgtgtgtgt gagtgcgtgc atggcctcag acacctgtgc tcccagcact    44760
gggcaggtat agacaggacg acctctgggg cttgctgacc anccgctcta actgaaccat    44820
tccagttccg tgtgctatgc cagctccaaa actaagctag agaatgattc aagaagacac    44880
caggcatcga cgttaggcat cgacgtttgg cctctaggca ccgtggacac acatagcaca    44940
ccccctcggt gcccttcttt taatacatgt acacaaaaga gagagagtgt ggtgaattaa    45000
aatgataagc agataatctg aacagcgcca agcaggaag gtgggcattg agattctagg     45060
gtcacacaga atctaaagca gagagaaggt aaagaaggca atctttctgc ggcctgaact    45120
gtacacacca cttactgact tctctttcag tgcgggacaa agtgtcaccg agctgcccag    45180
gcaggcctca cactcctggt cttaaactat cctcctcctc agacttctga gtagctcaga    45240
gtgcaggctc acaccaccct gcccagcttg ggatcatagc tttgaattat gaaatcacag    45300
agttgggtgt ggtggtacac acttgtagcc ctagggcttg agtggctgag gcaggttcac    45360
aggttcaagg ccagcctgag ctacataaca agaccttgtc tggaaaaaaa aataagaaag    45420
aatgacaaac ttattctttc tttttttagg aggagtaaaa cttggactgg gagatttcat    45480
tttctacagt gttctggttg gtaaggcctc agcaaccgcc agtggagact ggaacacaac    45540
catagcctgc tttgtagcca tactgatcgt aagtatatgc tggcaaaaac tggtcaggaa    45600
actgattctg catacctta tggtaatttt cttttaagtg tgtttgtaca cagatactgt      45660
ggcagtcgtg tgacagagag cattttttcct tccacttgag gcagggtctc tcagagaaca    45720
accttttggg agctggggct ttccttccac ctgtgggagg gtgtctcgtg ttttttaccat    45780 gagccaccgt gcactctggc ctattctaat tccccatctc tccataggac actaggattg    45840
caggtgggcg cccaccacat ccagcttctt acatgacttc cagggggtcaa actcaggtgt   45900 cgtgtttggg tggcaagtgc ttttttacctg ccgggccatc tttctagctc agagaattct   45960
cttttaattc caggcaggct aagaagcttt ataacgcttt tttaaaatgg ataatcagag    46020
cctgcctgag tatctctcca ctctggccac acattaaaat cagccgatgc ttccagccta    46080
gctgtgtctt ttctgcggaa tgtattgctg aggatgagcg aacaggagca ccaggtgcct    46140
gctgtattct cctcctgcac cagcctggtc tcagccctgt gctcaccttt gccccgccct    46200
tgggtagtta gttgtgagga gttcttaaga ggtctccagg aaactgtgag tacttctcat    46260
tagaaaccac tgtgagccag gcggtagtgg cacacacctt tgatcccagc acttgggaag    46320
tagaggcagg tggatctctg atgagcctgg tttacagagt gggttccagg acagccaggc    46380
actattcaca gaaattctgt ctcgaaaaaa aaggagggt ggggatgaaa tgaacagctt     46440
tgagagtcca gctgtatagg gctcaacaaa ggctgtcata gtccacgggc tgagtcagtg    46500
aatggccagt gcctttacat ctgatgcaca gcctgcacca tgcttgcttg gacagcagg     46560 tgtggagtga gaggggcaag cccagtgcat aagcccacat tctgtcttgc ttatgatggc    46620
tgtggctttc aaacatgact tagagcactg gatgtgttgg cgtgcacctt ttaatcctgg    46680
cattctggag gcaaaggcag gtggatctct gagttcaaga ccaaccttgt taagttctag    46740
gctacatagt gagagcccca tcttaaaaac aaaaacctga cttactaata acaaatgaac    46800
```

-continued

```
tatttcttat tgcttggagt tggggtatat agttcagctg tgagcgtgcc tgcatagtcc      46860
aaagccctgc attcaatctc caagcacata gtgcaggcac ggggccacat cccaacacta      46920
cggagatgaa aggagaaggg tccgaagttc aaggtcctcc ttagctatat gggggatctg      46980
aagccagctt gtctcaaaaa aaaggttttt tttccccttt aatccaggca ttatggtgca      47040
tacttacctc ctggcactta ggaggctgag ggagaaagat acagagtttg aagccagtct      47100
gggttgtgtg tatataaatg aagaaaaaaa acaacctctg cattttttt taaaatattt        47160 atttattaca tgtaaatata ctgtagctgt ctcccgacac accacaagag agagtcagat      47220
ctcattatgg atggttgtga gccaccatgt ggttgccggg aattgaactc aggacttcag      47280
aagagcagtc agtgcttctt aaccgctgag ccatctctcc agccccacca ctgcattttt       47340
gtagagggcc acactcccat gcacaggccc tgggctctgt cttcagcaca gatttttct        47400 tgttttttcca ttgcatctcc tcctgtcttc tctttcccgt ctccctcgag ccagctttcg     47460
ctgttgtcca gcctggtctc aggttctggc ctcagacagt cctgcctcag cctcctgagg      47520
agctgctgcg tgaccgtcag gcccagggcc acaagctacg cttttctctc gtgactccag      47580
agttcataag atgttgttgt aaaagttagg cctcaaggag agtattccct gagcgtggtg      47640
ctgatgctgc gtggcgtggg gatggtcctg agtgcgcctc tgtctccaca gggcctgtgc      47700
cttacattac tcctgctcgc catttcaag aaagcgttgc cagccctccc catctccatc       47760
accttcgggc tcgtgttcta cttcgccacg gattaccttg tgcagccctt catggaccaa      47820
cttgcattcc atcagttta tatctagcct ttctgcagtt agaacatgga tgtttcttct       47880
ttgattatca aaacacaaa acagagagc aagcccgagg aggagactgg tgactttcct         47940
gtgtcctcag ctaacaaagg caggactcca gctggacttc tgcagcttcc ttccgagtct      48000
ccctagccac ccgcactact ggactgtgga aggaagcgtc tacagagaac ggtttccaac      48060
atccatcgct gcagcagacg gtgtccctca gtgacttgag agacaaggac aaggaaatgt     48120
gctgggccaa ggagctgccg tgctctgcta gctttgaccc gtgggcatgg agatttaccc      48180
gcactgtgaa ctctctaaag gttaaacaaa gtgaggtgaa ccaaacagag ctgccatctt      48240
ccacaccatg ttggaaataa aacacgtcct agctgaaccc ttactgtcca ggaagttccg     48300
tgtggaagtg gcactgggcc gggcctccct ctcaggctcc tttgctgccc acttgtaagt      48360
ttaaataagg acaccgccct acacaaacct caccctgtca catcagtgac tctgaccact     48420
tttgttctca aactctctca ctattatctg tggttgccgt ttcttcccaa ggccagcctg      48480
gacgaatttg gggttgctct atcctgagag ttgtaacctc aacttccaaa gtttatattt      48540
tcttgaaatg atggatctat tgctcaacag tccctgtcat ccttaagtga cttctgggtt      48600
tcccacaaat tcctcacttt tagacacact ctaagcttac ttctggcctg natgcttcct      48660
ctccctgtct ctcccttgcc ccacagcggt tccctgacag cagacaaggc agctctggga     48720
ggtagctagt atccaataac ccaggggttt cctcatgtga tgcaaatact acgtgtccaa     48780
ccaatcagtg ctgtcaacgg gctgccatag ctccttcgat ggcaaatagg atgtgtgccc      48840
aaagaattaa agcgatgagt ggctggtgaa gcgctctctg tcctggctgg ttttttgtca    48900
ccgcaatcca ctgccaaagg cagaatttaa actaggggct gaaggatagc tccgagtaat    48960
gtccaatgct ggga                                                       48974
```

<210> SEQ ID NO 18
<211> LENGTH: 157
<212> TYPE: DNA
<213> ORGANISM: Mus musculus

<400> SEQUENCE: 18

| | | | | | |
|---|---|---|---|---|---|
| cccctcccgg | gtctaggggc | caacgtcgcc | gaggccggaa | gttgcgacac | cggtgagacc | 60 |
| tctagggcgg | ggcctaggac | gacctgctcc | gtgggccgcg | agtattcgtc | ggaaacaaaa | 120 |
| cagcggcagc | tgaggcggaa | acctaggctg | cgagccg | | | 157 |

<210> SEQ ID NO 19
<211> LENGTH: 157
<212> TYPE: DNA
<213> ORGANISM: Homo sapiens

<400> SEQUENCE: 19

| | | | | | |
|---|---|---|---|---|---|
| ctcctccgtg | ggccggccgc | caacgacgcc | agagccggaa | atgacgacaa | cggtgagggt | 60 |
| tctcgggcgg | ggcctgggac | aggcagctcc | ggggtccgcg | gtttcacatc | ggaaacaaaa | 120 |
| cagcggctgg | tctggaagga | acctgagcta | cgacccg | | | 157 |

<210> SEQ ID NO 20
<211> LENGTH: 109
<212> TYPE: DNA
<213> ORGANISM: Mus musculus

<400> SEQUENCE: 20

| | | | | | |
|---|---|---|---|---|---|
| ggcctcgcga | tcagagtgga | gctagagata | gaggaagcgc | cctaggctgg | gtcgccttga | 60 |
| gcaactggtg | aaactctgcg | tctggtgccc | cgagtgtgtc | atagtccag | | 109 |

<210> SEQ ID NO 21
<211> LENGTH: 109
<212> TYPE: DNA
<213> ORGANISM: Homo sapiens

<400> SEQUENCE: 21

| | | | | | |
|---|---|---|---|---|---|
| gccgtcgtaa | ctggagtgga | gtaggagaaa | gaggaagctt | cttgggctgg | gtctgcttga | 60 |
| gcaactggtg | aaactccgcg | cctcacgccc | cgggtgtgtc | cttgtccag | | 109 |

<210> SEQ ID NO 22
<211> LENGTH: 1100
<212> TYPE: DNA
<213> ORGANISM: Mus musculus

<400> SEQUENCE: 22

| | | | | | |
|---|---|---|---|---|---|
| aaaatcaaga | taggaaacat | tctttgcttt | ctagaagctt | gccatctggg | aagactttca | 60 |
| gactcggaac | ctagactaat | aggatatttc | tcaggttctg | tttacccacc | aatcgctttg | 120 |
| gtttattgag | agtacaaaca | gtaaatttta | tccgttttga | ggaactgttc | aaataaatac | 180 |
| tgtggagaaa | tgggaagtgt | tggatttaaa | atgtcactac | aaaacaaggc | acggtgtccc | 240 |
| cacacatgga | aaccaaataa | ataggttcaa | gcccatcctt | tcctacaagg | tatgtttgat | 300 |
| accggcaggg | aacgctcgaa | tcgcagtctc | aaccaaaaac | aagggaaaat | gtcacttgta | 360 |
| gactggaaga | acgctagacg | cgcctcaaac | cctagagagg | cctcaggtcg | cgcacatcct | 420 |
| tacatctatg | cgagtggatt | aggccagctc | cagcccagc | cctcgtggcc | tgcgcgcgcc | 480 |
| accggaagct | ccgtcccctc | ccgggtctag | ggccaacgt | cgccgaggcc | ggaagttgcg | 540 |
| acaccggtga | gacctctagg | gcggggccta | ggacgacctg | ctccgtgggc | gcgagtatt | 600 |
| cgtcggaaac | aaaacagcgg | cagctgaggc | ggaaacctag | gctgcgagcc | ggccgccgg | 660 |
| gcgcggagag | agaaggtgcg | tgcccagggt | gtgcggggcg | gagggtgtct | ctgccggtcg | 720 |

-continued

```
tgttcaccgt cgcctgcctg ccgggggtcc gggcgggcct gtgtctccga gggccgcgct      780
gcgggcgtct ctagggatga ggggcggggt ccaggcgggc ggagatcgag gaacccgcg       840 tgggaaacgg ggtgaagccg gtttctcgga acccagccgg ggccagactg agagcagcct     900
tctccgagct ttggtacccc ggaagtgctg gcttcccgg gcggccggga gcagatggct     960
ggcatcaggg gtggcctctc gatcagagtg gagctagaga tagaggaagc gccctaggct     1020
gggtcgcctt gagcaactgg tgaaactctg cgtctggtgc cccgagtgtg tcatagtcca     1080
gaagtgagtg agtggcactc                                                   1100
```

PRESENILIN-1 GENE PROMOTER

This invention was made with Government support under Grant RO1 AG-13839 from the National Institutes of health. The Government has certain rights to this invention.

FIELD OF THE INVENTION

This invention relates to genomic Presinilin-1 gene constructs, and the regulatory regions thereof, and recombinant DNA constructs employing the same.

BACKGROUND OF THE INVENTION

Alzheimer's disease (AD) is a devastating neurological disorder and the most common cause of dementia. The genetics of this disorder suggest that multiple genes are involved. To date, mutations in four genes have been found to be associated with Alzheimer's disease phenotypes including the Amyloid Precursor Protein (APP) gene on chromosome 21 (Citron, M. et al., Nature 360, 672–674 (1992); Suzuki, N. et al., Science 264, 1336–1340 (1994)), the Apolipoprotein-E (APOE) gene on chromosome 19 (Corder, E. H. et al., Science 261, 921–923 (1993); Corder, E. H. et al., Nat. Genet. 7, 180–184 (1994); Strittmatter, W. J. et al., Proc. Natl. Acad. Sci. U.S.A. 90, 1977–81 (1993)), the Presenilin-1 (PS-1) gene on chromosome 14 (Sherrington, R. et al., Nature 375, 754–760 (1995)) and the Presenilin-2 (PS-2) gene on chromosome 1 (Levy-Lahad, E.et al., Science 269, 973–977 (1995)). An unknown gene on chromosome 12 appears to associate with a large percentage of late-onset AD patients (Stephanson, J. J Am. Med. Asoc. 277, 775 (1997)). The majority of familial Alzheimer's disease cases are associated with mutations in the PS-1. To date, over 30 independent mutations in the PS-1 gene have been described in unrelated Alzheimer's families displaying an early-age-of-onset phenotype. Most of these mutations are missense mutations that result in single amino acid changes (Wasco, W. et al., Nat. med. 1, 848 (1995); Alzheimer's Disease Collaborative Group, Nat. Genet. 11, 219–222 (1995); Campion, D. et al., Hum. Mol. Genet. 4, 2373–2377 (1995); Cruts, M.et al., Hum. Mol. Genet. 4, 2363–2371 (1995); Boteva, K. et al., Lancet 347, 130–131 (1996); Rossor, M. et al., Lancet 347, 1560 (1996); Kamino, K. et al., Neurosci. Let. 208, 195–198 (1996)).

Deletions found in Exons 4 and 9 cause additional mutations as do several truncations of the RNA transcripts arising by differential splicing (Perez-Tur, J. et al., Neuroreport. 7, 297–301 (1995).). Although clustering of these mutations within the protein suggests the location of functionally important domains, the exact function of Presenilin proteins is a matter of active investigation.

One approach to find gene function is to study the regulation of PS-1 gene expression. Using in situ hybridization, we and others demonstrate that PS-1 mRNA is most highly expressed in neurons of the brain (Koracs, D. M. et al., Nat. Med. 2, 224–229 (1996)). Immunohistochemistry revealed that the PS-1 protein was abundant in neurons, but was also associated with amyloid plaques and some glial cell types (Scheuner, D. et al., Nat. Med. 2, 864–870 (1996); Lah, J. et al., J. Neurosci. 17, 1971–1980 (1997)). In contrast, Sherrington et al. reported that PS-1 mRNA is widely expressed in a variety of organs throughout the body (Nature 375, 754–760 (1995)). This raises the question as to why mutations in the PS-1 gene product appear to confer a disease state in familial Alzheimer's patients without apparent effect on their peripheral organs. The situation is further compounded because PS-1 mRNA and protein levels from FAD patients and age-matched healthy controls have not been reported, leaving open the possibility that aberrant regulation of PS-1 gene expression further contributes to the disease state.

Mutations in the PS-1 gene's promoter and non-protein encoding regions are not known and reports on the gene's wild-type sequence are lacking. Similarly, no functional analysis of the gene's ability to promote transcription have been reported. Combined with recent reports that PS-1 knockout mice are embryonic lethal ( Shen, J. et al., Cell 89, 629–639 (1997)), knowledge of the PS-1 gene sequence and its transcriptional regulation should be important clues that help to identify PS-1 function in both noon and diseased states.

SUMMARY OF THE INVENTION

We herein described a complete sequence of the mouse Presenilin-1 gene. This sequence has shown that there are two independent transcription start sites. Functional testing of the DNA regions surrounding these start sites showed that they both were apparently controlled by a single, major promoter that includes the +1 position of Exon 1A. This promoter was also quite interesting because it is mostly active in neuron-like cells. Further characterization can now progress to a complete description of those positive and negative DNA elements and transcription factors which function to control Presenilin-1 gene expression.

A first aspect of the present invention is, accordingly, an isolated DNA molecule that directs neuron-specific transcription of a downstream heterologous DNA segment in a mammalian cell, said isolated DNA molecule having a sequence selected from the group consisting of:

(a) the sequence spanning position –327 to position –206 of the mouse genomic Presenilin-1 gene (with position +1 indicating the transcription start site of exon 1A);

(b) the sequence spanning position –449 to position +1171 of the mouse genomic Presenilin-1 gene;

(c) the sequence spanning position –9 to position +16, of the mouse genomic Presenilin-1 gene (the sequence AGGCCGGAAGTTGCGACACCGGTGA (SEQ ID NO:1)); and (d) DNA sequences that hybridize to isolated DNA having a sequence of (a), (b), or (c) above, and which direct neuron specific transcription of a downstream heterologous DNA segment in a mammalian cell.

By "neuron specific" is meant any level of specificity, so long as the downstream heterologous DNA is preferentially transcribed or expressed in a neuron. By "neuron" is meant an excitable cell that sends a signal, as is well known in the art (e.g., neurons of the brain cortex).

A second aspect of the present invention is a DNA constrict comprising an expression cassette, which contains, in the 5' to 3' direction, a promoter segment consisting of a DNA sequence as given above, and a heterologous DNA segment positioned downstream from said promoter segment and operatively associated therewith.

A third aspect of the present invention is a nerve cell containing a DNA construct as described above.

A fourth aspect of the present invention is a method of making a transgenic non-human animal. The method comprises transforming an animal cell with an expression cassette as described above, and then regenerating an animal from the transformed animal cell.

A fifth aspect of the present invention is a transgenic non-human animal, wherein some or all of the cells of the animal containing a heterologous expression cassette as described above.

BRIEF DESCRIPTION OF THE DRAWINGS

FIG. 1. Structure of Three Different Presenilin-1 Transcripts from Mouse Brain. The cloned products of 5'-RACE of mouse brain cDNA and DNA sequencing revealed the presence of three independent transcripts (A, B and C) which appear to derive from two unique transcription start sites marked by the vertical arrows. The distance between two transcription start sites is 410 Bp. The sizes of Exon 1A, 1B and 1C are 141 Bp, 371 Bp and 139 Bp, respectively.

FIGS. 2A, 2B, and 2C. Cloning and Sequencing Strategy Elucidates the Mouse Presenilli-1 Gene's Exon-Intron Structure.

FIG. 2A. Screening Strategy: "Screening-A" utilized a fragment of the mouse PS-1 cDNA as Probe A (filled box) to identify lambda phage clones of the mouse PS-1 genomic DNA (represented as double lines). "Screening-B" utilized PCR primers to identify a P1 clone of the mouse PS-1 gene, P1-10809, as represented by the hatched horizontal box.

FIG. 2B. Sequencing Strategy: Lambda phage clones and P1-10809 were restricted and subcloned into pBluescript II KS(+) vector. Thick lines correspond to individual plasmid subclones from corresponding regions of PS-1 genomic DNA found in P1-10809. Double arrows represent PCR products from P1-10809 template which were sequenced directly. Restriction endonucleases abbreviated as: H, Hind III; E, EcoR I; N, Not I; X, XhoI I.

FIG. 2C. Exon-Intron Structure of the Mouse PS-1 Gene: Exons are boxed and double lines represent Introns. Filled boxes and open boxes correspond to the protein coding and untranslated regions, respectively. The translation start codon ATG begins at position +11,420, the translation termination codon TAG is at +45,627 and the putative polyadenylation signal (AATTAA) is at position +46,612.

FIG. 3. Comparison of the Mouse and Human Presenilin-1 Promoters. Mouse PS-1 transcription begins with "G" at position +1 of Exon 1A and human PS-1 transcription begins with "A" (Data not shown.). By DNA sequence similarity searching with BLAST network service available from National Center Biotechnology Information, regions of mouse/human homology are found around the transcription iniation sites for both genes. Consensus binding sites for the transcription factors ETS1 and SP1 are underlined and are conserved in both mouse and human genes.

FIG. 4. Nucleotide Sequence of the Mouse PS-1 Promoter Region. The sequence of mouse PS-1 gene flanking the two transcription initiation sites, marked with vertical arrows, is displayed. Some restriction endonuclease sites are underlined and various promoter elements are boxed and labeled. Exon 1A and Exon 1B are double-underlined.

FIG. 5A. Structural Organization of PS-1 Promoter: Top line represents the region of the PS-1 gene which was analyzed for promoter activity where boxes for Exon 1A and Exon 1B are labeled. Open boxes represent genomic DNA fragments corresponding to the mouse PS-1 gene (top line) which were cloned upstream of the Firefly luciferase reporter gene in the plasmid pGL3-Basic (Promega). Open boxes are labeled on the left with the name of the promoter-reporter plasmid as LUC # and with a nucleotide number of the 5' end of the fragment based on +1 being the "G" at the beginning of Exon 1A. Letters above the open box refer to a restriction enzyme cleavage site. Numbers to the immediate right of the open box denote the 3' end of the promoter fragment. The numbers on the left hand side are the percentage of Relative Luciferase Activity (%RLA) calculated as described in Materials and Methods followed by the number of times that construct has been transfected into cells and its activity measured which is in parentheses.

FIG. 5B. Fine Structure Map of the PS-1 Promoter and Promoter-Reporter Construct Activity Strategy. Top line represents the region of the PS-1 gene with putative promoter elements, Exon 1A, Exon 1B and restriction enzyme site positions labeled. Open boxes of promoter-reporter constructs are as in (A). Letters above the open box refer to the end of the promoter fragment shown in FIG. 3.

DETAILED DESCRIPTION OF THE INVENTION

Figure 2A:
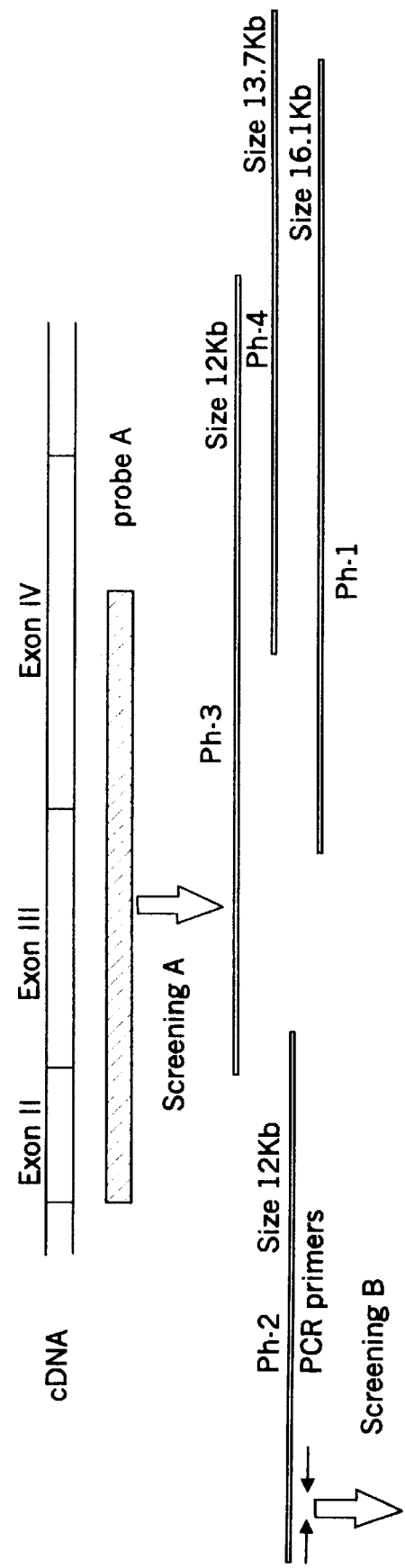

Nucleotide sequences are presented herein by single strand only, in the 5' to 3' direction, from left to right. Nucleotides are represented herein in the manner recommended by the IUPAC-IUB Biochemical Nomenclature Commission.

Specific examples of neuron specific promoters of the present invention include, but are not limited to, DNA molecules that comprise mouse Presenilin-1 gene promoter segments from position:

−440 to +91;
−352 to +91;
−327 to +91;
−276 to +91;
−261 to +91;
−215 to +91;
−192 to +91;
−124 to +91;
−87 to +91; and
−32 to +91.

From position:

−276 to +519;
−276 to +206;
−276 to +148; and
−276 to +41.

And from position:

−87 to +41;

−9 to +16; and
−327 to +206.

The corresponding fragments from the Presenilin-1 gene of other mammalian species, such as rat, cat, dog, monkey, or human, may also be employed to carry out the present invention., as discussed in greater detail below.

Promoters of the present invention may be of any animal species of origin, but are preferably of mammalian origin (e.g., mouse, rat, cat, dog, monkey, human). Promoters used to carry out the present invention are, in general, substantially homologous to the mouse segments described above. As used herein, such regions are "substantially homologous" when their DNA binding required for promoter function are homologous to eh various mouse promoter segments described herein. In general, such regions are at least 75%, and more preferably 80%, 85%, 90%, or even 95% homologous to the various mouse promoter segments described herein. It will be apparent that other sequence fragments of the regions flanking the foregoing sequences, or minor additions, deletions or substitutions thereto, can be prepared which will also carry out the function of a Presenilin-1 gene promoter. They may also be identified by their binding to specific transcription factor proteins and/or their function to promote transcription.

Other DNA segments such as naturally occurring DNA segments or mammalian DNA segments, which encode neuron-specific gene promoters can be identified by their binding, or hybridization, to fragments as described above. Hybridization conditions which will permit such DNA sequence to hybridize to a DNA sequence as given herein are known in the art. For example, hybridization of such sequences to the DNA disclosed herein may be carried out in 25% formamide, 5×SSC, 5×Denhardt's solution, with 100 µg/ml of single stranded DNA and 5% dextran sulfate at 42° C., with wash conditions of 25% formamide, 5×SSC, 0.1% SDS at 42° C. for 15 minutes, to allow hybridization of sequences of about 60% homology. More stringent conditions are represented by a wash stringency of 0.3M NaCl, 0.03M sodium citrate, 0.1% SDS at 60° C. or even 70° C. using a standard hybridization assay (See Sambrook et al., *Molecular Cloning, A Laboratory Manual* (2d Ed. 1989) (Cold Spring Harbor Laboratory)).

The term "operatively associated" as used herein refers to DNA sequences contained within a single DNA molecule that are associated so that the function of one is affected by the other. Thus, a promoter is operatively associated with a gene (or other DNA of interest) when it is capable of affecting the expression of that gene (i.e., the gene is under the transcriptional control of the promoter). The promoter is said to be "upstream" from the gene (or other DNA of interest), which is in turn said to be "downstream" from the promoter.

DNA constructs, or "expression cassettes," of the present invention include, 5' to 3' in the direction of transcription, a promoter of the present invention, a heterologous DNA segment operatively associated with the promoter, and, optionally, transcriptional and translational termination regions such as a termination signal and a polyadenylation signal. All of these regulatory regions should be capable of operating in the transformed cells. The 3' termination region may be derived from the same gene as the transcriptional initiation region or from a different gene. The expression cassette may be provided in a DNA construct that also has at least one replication system.

As used herein, the term "heterologous gene" or "heterologous DNA segment" means a gene (or DNA segment) which is used to transform a cell by genetic engineering techniques, and which may not occur naturally in the cell. Structural genes are those portions of a genes which comprise a DNA segment coding for a protein, polypeptide, or portion thereof, possibly including a ribosome binding site and/or a translational start codon, but lacking a promoter. The term can also refer to copies of a structural gene naturally found within a cell but artificially introduced. Structural genes may encode a protein not normally found in the cell type into which the gene is introduced or in combination with the promoter to which it is operationally associated. As used herein, the term heterologous DNA segment also includes DNA segments coding for non-protein products, such as ribozymes or anti-sense RNAs (see, e.g., U.S. Pat. No. 4,801,540).

The various fragments comprising the various constructs, expression cassettes, markers and the like, may be introduced consecutively by restriction enzyme cleavage of an appropriate replication system and insertion of the particular construct or fragment into the available site. After ligation and cloning, the DNA construct may be isolated for further manipulation. All of these techniques are amply exemplified in the literature. See, e.g., Maniatis et al., *Molecular Cloning: A Laboratory Manual* (Cold Spring Harbor Laboratory, Cold Spring Harbor, N.Y. 1982).

Promoters and the various constructs of the present invention have a variety of different uses. Nerve cells grown in culture may be transformed with constructs of the present invention and the heterologous DNA expressed therein to produce a protein or a peptide, and the protein or peptide then collected for subsequent use (for example, the protein or peptide could encode an antigen, which is used directly in diagnostic assays, or which is injected into an animal to produce antibodies thereto, which antibodies are used in diagnostic assays). Transgenic animals may be produced with the constructs of the invention, as discussed in greater detail below. The promoters may be used in vectors that comprise gene therapy vectors (e.g., viral vectors such as herpesvirus vectors and RNA viruses such as retroviruse (wherein the promoter segment and the heterologous segment exist as an RNA transcript of the DNA which is inserted into the host cell as a DNA transcript, or in the case of retroviruses as a provirus)) where the heterologous DNA encodes a therapeutic agent (e.g., ApoE2 or ApoE3; nerve growth factor, ciliary neurotrophic factor, etc.); and where preferential expression of the heterologous DNA in nerve cells is desired . Numerous other uses for promoters of the instant invention will be readily apparent to those skilled in the art.

As noted above, a method of making a transgenic animal is also an aspect of the present invention. The method can be carried out on any suitable animal subject, but is preferably carried out with non-human mammals. Murine species or rodents (e.g., mice, rats) are particularly preferred.

The method comprises transforming an animal cell with an expression cassette as described above, in an animal transformation vector, and then regenerating a transgenic animal from the transformed animal cell. The transformation step may be carried out by any suitable means, as discussed in detail below, and the regeneration step may also be carried out by any suitable means, as also discussed in detail below. Where chimeric animals are produced by the process, animals in which all cells (e.g., including both somatic cells and germ cells) are transformed (and in which the expression cassette described above is stably integrated into the genome of the cells) may be regenerated from chimeric animals having transformed germ cells, as is known in the art.

The production of transgenic animals can be carried out by any suitable technique, such as pronuclear microinjection, infection of embryos with retroviruses, embryonic stem cell-mediated techniques, transfer of entire chromosomal segments and gamete transfection in conjunction with in vitro fertilization, etc. See generally Charles River Laboratories, *Transgenic Animal Science: Principles and Methods* (Summer 1991).

Transgenic animals that carry an expression cassette of the invention can be produced by the genetic transformation of zygotes, as described in T. Wagner et al., U.S. Pat. No. 4,873,191 (applicant intends that the disclosure of all U.S. Patent References cited herein be incorporated herein by reference).

In another technique, a pluripotent embryonic stem cell from the species to be transformed may be derived, the expression cassette inserted into the stem cell, and one or more of the stem cells inserted into an early embryo such as a blastocyst of the animal to be transformed, and the animal raised to birth in a suitable female host (e.g., M. Evans, PCT Application WO90/03432). Methods of producing transgenic animals by subjecting a mixture of DNA and the embryo to an electric discharge are described in U.S. Pat. No. 5,567,607 to X. Zhao et al. Mammalian expression vectors are described in U.S. Pat. No. 5,627,033 to J. Smith et al.

Animals of the present invention are useful as laboratory models for studying the function of the Presenilin-1 gene, for studying the etiology of Alzheimer's disease, and for studying the activity of various drugs and drug candidates in treating Alzheimer's disease. In such animals the endogeneous Presenilin-1 gene may be active or inactive. The endogeneous Presenilin-1 gene may be inactivated by means of a "knock-out" of the Presenilin-1 gene in accordance with known techniques, such as homologous recombination. See, e.g., O. Smithes, *Nature* 317, 320 (1985).

In the Examples set forth below, the abbreviation used are: Bp, base pairs; PEA-3, polyoma virus enhancer activator-3; PS-1, presenilin-1; 5'-RACE, rapid amplification of 5'-cDNA ends; N2a, Neuro2a cells; P19N, neuron-like differentiated P19 cells; P19M, muscle-like differentiated P19 cells; RLA, relative luciferase activity; IRLA, Index of relative luciferase activity.

EXPERIMENTAL PROCEDURES

Isolation and characterization of genomic clones— Labeled oligonucleotides and PCR products of the mouse PS-1 cDNA were used as probes to screen mouse libraries for genomic PS-1 clones. Based on the mouse PS-1 cDNA sequence (Genbank Accession #L42177), an upstream primer of sequence

5'-CGGAGAGAGAAGGAACCAAC-3' (SEQ ID NO: 2)

and a downstream primer of sequence

5'-TCAGCTCTTCGTCTTCCTCCTCATC-3' (SEQ ID NO: 3)

were used with Quick Clone Mouse Brain cDNA (Clontech) as template to amplify a portion of the mouse PS-1 cDNA by polymerase chain reaction (PCR). Amplification reactions were performed in 100 μl volume containing 1×PCR buffer II (Perkin Elmer), MgCl$_2$ (1.5mM), dATP, dGTP, dCTP and dTTP (0.2 mM each, Perkin Elmer), DNA primers at 0.5 μM, 1 μl cDNA template (0.1 ng) and Ampli-Taq DNA polymerase (5 Units, Perkin Elmer). The reaction cycle was 95° C. for 1 minute, 50° C. for 1 minute and 72° C. for 2 minutes for a t 30 cycles. This PCR product was gel purified and labelled with alpha-$^{32}$P-dCTP and a Random Primers DNA Labelling System (Gibco). Labelled probe was used to conventially screen a mouse strain 129/SVJ genomic library in Lambda Fix-II vector (Stratagene) as described (Sambrook, J. Fritsch, E. F., and Maniatis, T, Molecular cloning: a laboratory manual, Cold Spring Harbor Laboratory Press, Cold Spring Harbor, N.Y. (1989).). Screening identified four independent phage clones designated Ph-1, Ph-2, Ph-3 and Ph-4 (FIG. 2). Following digestion with Not I and/or EcoRI, restriction enzyme fragments were subcloned into pBluescript-II-KS(+) phagemid vector (Stratagene) using a DNA ligation kit (Stratagene). DNA sequence was determined using an Applied BioSystems model 373A automated DNA sequencer with dye terminator chemistry and protocols recommended by the manufacturer. Additional oligonucleotide probes from the 5'-untranslated region of the mouse PS-1 cDNA were labeled with $^{32}$P-ATP and T4-polynucleotide kinase and used to identify plasmid subclones by hybridization. Based on the partial sequence of phage clone Ph-2, the PCR primers 1C-US-for

GATCACAGTCTAGGTTGCTGGTGTG (SEQ ID NO: 4)

and 1C-US-rev

TGGGGCAAGGG ACACAAATAAG (SEQ ID NO: 5)

were used to further screen a mouse ES-129/SVJ genomic library in a P1 vector (Genome Systems Inc.) by PCR. Of the three P1 clones identified, P1-10809 was digested with EcoRI or Hind III and these restriction enzyme fragments subcloned and sequenced as described above.

5'-Rapid Amplification of cDNA Ends or RACE:—The 5' end of PS-1 cDNA was identified using mouse-brain Marathon-Ready cDNA (male BALB/c, 9–11 weeks of age, Clontech). Briefly, a 50 μl PCR reaction containing 0.2 μM of a PS-1-specific reverse primer:

TGGCTCAGGGTTGTCAAGTC (SEQ ID NO: 6)

0.2 μM of the Clontech AP1 adaptor primer:

CCATCCTAATACGACTCACTATAGGGC (SEQ ID NO: 7)

2.5 ng Marathon-Ready CDNA, 1×PCR buffer (Gibco), MgCl$_2$ (1.5 mM), DMSO (5%), dATP, dGTP, dCTP and dTTP (0.2 mM each), and Taq DNA polymerase (5 Units, Gibco) was used with a reaction cycle of 95° C. for 45 seconds, 55° C. for 30 seconds and 72° C. for 90 seconds for a total of 30 cycles in the first amplification step. The 100 μl second PCR amplification step contained 0.5 μM of a mouse PS1-specific reverse primer, 151–130-reverse:

CAAACCTCTTGGGATTCTTTC (SEQ ID NO: 8)

and 0.5 μM of the nested Clontech adaptor primer AP2

ACTCACTATAGGGCTCGAGCGGC (SEQ ID NO: 9)

and 0.01 μl of the first PCR amplification, 1×PCR buffer (Gibco), MgCl$_2$ (1.5 mM), DMSO (5%), dATP, dGTP, dCTP and dTTP (0.2 mM each) and Taq DNA polymerase (5 Units, Gibco) with the same cycling parameters as in the first amplification step. In some second PCR reactions, the PS-1 specific reverse primer 101–80-reverse:

AAGACCTCGAAGGGCTGCTGTC (SEQ ID NO: 10)

was used. RACE amplification products were electrophoresed on 2% agarose gels run in TAE, visualized with ethidium bromide and ultraviolet light, extracted from the gel matrix with a Wizard PCR Preps DNA Purification System (Promega), ligated into a pGEM-T vector (Promega) and transformed into competent DH5-alpha bacterial cells (Gibco). Ampicillin resistant colonies were characterized by restriction enzyme digestion, PCR amplification with a variety of primer combinations and DNA sequencing as above.

Computation of Sequence Similarities:—Comparison of the mouse PS-1 promoter with other eukaryotic promoter sequences were performed using the BLAST network service and the Eukaryotic Promoter database (EPD) Release 45 available from the National Center for Biotechnology Information.

Construction of PS-1 Promoter-Firefly Luciferase Reporters:—Mouse genomic DNA fragments containing portions of the putative PS-1 promoter were subcloned into the promoterless pGL3-basic vector (Promega) upstream of the firefly luciferase gene. Based on the sequence of genomic DNA, PCR primers were designed to incorporate XhoI I sites into the forward primers and Hind III sites into the reverse primers. These primers corresponding to different locations in the genomic DNA (see FIG. 2) were used to PCR amplify fragments as above which were purified with a Wizard Purification System (Promega), digested with the appropriate restriction enzymes and repurified with the Wizard kit. Cleaved PCR products were ligated into pGL3 plasmid cleaved with the same restriction enzymes, transformed into competent bacteria and clones containing plasmids with inserts verified by DNA sequencing.

Eucaryotic Cell Culture and Transfection.—Mouse Neuro2a-neuroblastoma cells, mouse P19-embryonal carcinoma and mouse NIH/3T3 fibroblast cells were obtained from the American Type Culture Collection (ATCC). Neuro2a cells were routinely propagated in Minimal Essential Medium with Earle'salt (Gibco) plus 10% fetal calf serum (Hyclone) plus 0.1 mM non-essential amono acids (Gibco). P19 cells were routinely propagated in alpha-MEM (Gibco) plus 2.5% fetal calf serum plus 7.5% bovine serum (Hyclone). Differentiation of P19 cells to neuron-like cells followed treatment with 0.5 $\mu$M trans-retinoic acid (Jones-Villeneuve, E. et al., *Mol. Cell. Biol.* 3, 2271–2279 (1983)). Differentiation of P19 cells to muscle-like cells followed treatment with 1% dimethylsulfoxide (Edwards, M. et al., *Mol. Cell. Biol.* 3, 2280–2286 (1983).). NIH/3T3 cells were routinely propagated in DMEM (Gibco) plus 10% fetal calf serum.

For transient transfection, Neuro2a, P19, retinoic acid treated-P19, DMSO-treated P19 and NIH/3T3 cells were plated in 6 well tissue culture dishes at $9 \times 10^4$ cells per well and allowed to recover for one day. Cells containing PS-1-promoter-reporter constructs were then co-transfected with 0.3 pmole of one of the Promoter-Firefly Luciferase plasmid constructs, pGL3 Basic vector or pGL3 Promoter plasmid (Promega), which contains an SV40 promoter upstream of the firefly luciferase gene, and 0.3 pmole of pRL-TK plasmid (Promega), which contains an herpes simplex virus thymidine kinase promoter upstream of the Renilla luciferase gene, using the Lipofectin procedure (Gibco) as described in the manufacture's protocol.

Relative Luciferase Activity Measures:—Transfected cells were cultured for 24 hours, washed twice with 2 ml of $Ca^{2+}$ and $Mg^{2+}$ free PBS and lysed with Passive Lysis Buffer (Promega). Firefly luciferase and Renilla (sea pansy) luciferase activities were measured sequentially using a Dual-Luciferase Reporter Assay System (Promega) and a model TD-20E Luminometer (Turner Design). After measuring the Firefly luciferase signal ($LA_F$) and the Renilla (sea pansy) luciferase signal ($LA_R$), the Relative Luciferase Activity (RLA) was calculated as: $RLA = LA_F / LA_R$, where relative RLA was calculated as a percentage, ie. $\%RLA = RLA/(RLA)_{max}$. To compare the Relative Luciferase Activity in one cell line with another, an Index of Relative Luciferase Activity was calculated as: $IRLA = RLA/RLA_{SV40}$ where $RLA_{SV40}$ is the ratio of Firefly luciferase signal with an SV40 promoter in pGL3 divided by the Renilla luciferase signal in pRL-TK.

Results

RACE Detects Multiple Transcripts.—As a prelude to cloning the PS-1 promoter, the exact 5' end of mouse brain PS-1 mRNA was identified by the rapid amplification of cDNA ends (RACE) technique. 5'-RACE with the anti-sense oligonucleotide "101–80-reverse" found in exon 2 of mouse PS-1, gives a major broad band of 210 bp's and a minor band of 430 bp's from single-stranded cDNA templates complementary to mouse brain mRNA (Marathon Ready cDNA, Clontech, data not shown). Each of these bands was isolated from agarose gels, subcloned into the pGEM-T vector (Promega) and sequenced. Sequencing revealed the presence of three different PS-1 transcripts which appear to derive from 2 unique transcriptional start sites (FIG. 1). This information suggests that the PS-1 gene may contain 2 promoters and that differential splicing generates multiple transcripts.

Isolation of the Mouse PS-1 Gene.—A mouse genomic DNA library in Lambda-FIX II was screened with Probe A, a $^{32}$P-labeled PCR probe corresponding to Exons 2, 3 and 4 of the murine PS-1 cDNA clone (FIG. 2A). Of the positively hybridizing phage clones, four were selected for restriction mapping with EcoRI and Not I as shown in FIG. 2B. Only one phage clone, Ph-2 (FIG. 2B) hybridized to oligonucleotides from the 5'-untranslated region of the mouse PS-1 cDNA. Primers from the phage arms allowed sequencing into the genomic DNA insert. The insert's sequence allowed the PCR primer pair "1C-US-forward and 1C-US-reverse" to be chosen and used to identify a P1 clone of the mouse PS-1 genomic DNA as shown in FIG. 2A. Clone P1-10809 was identified through a positive PCR reaction product with these primers and hybridization to the PS-1 CDNA fragment probe A (FIG. 2). P1-10809 was then restricted, mapped and its entire sequence sublconed into multiple pBluescript-II-KS-(+) plasmid vectors as shown by the thick lines in FIG. 2B. Each subclone was sequenced on an Applied Biosystems 373A automated DNA sequencing machine using protocols supplied by the manufacturer.

Characterization of the PS-1 Gene's Exon-Intron Structure.—The sequence of almost 50 kBp of the P1-10809 clone was compared to the mouse PS-1 cDNA sequence and regions of homology aligned with the MacVector DNA analysis program (IBI, New Haven, CT). The first nucleotide on the 5' end of the RNA transcript is usually designated as nucleotide +1 of exon 1 of a gene. In our case, PS-1 appears to have two different 5' end-sequences which are associated with three different length RNA transcripts which we named Transcript-A, Transcript-B and Transcript-C. The alignment of Transcript-A with genomic sequence shows that a "G", designated conventionally as position +1 in Exon 1, corresponds to the transcription start site. The Presenilin gene's Exon 1A extends from position +1 to +141 which is spliced to Exon 2 whose 5' end begins at position +11,210 to give Transcript-A. The alignment of Transcript-B with genomic DNA shows that a "C" at position +411 corresponds to the alternative transcription start site. We define this second start site as beginning in Exon 1B which extends from position +411 to +781 and is spliced to Exon 2 (position +11,210) to give Transcript-B. The alignment of Transcript-C with genomic DNA shows the same "C" at position +411 as the alternative transcription start site. We define Exon 1C as extending from position +411 to +549 which is spliced to Exon 2 at position +11,210 to give Transcript-C. As shown in FIG. 2C and summarized in Table 1, Exon 1A, Exon 1B, Exon 1C and Exon 2, together with a portion of Exon 3, comprise the 5' untranslated regions of PS-1 RNA transcripts.

TABLE 1

Numbering Scheme for the Mouse PS-1 Gene's Exon-Intron Structure.[1]

|  | Size | Position |
|---|---|---|
| Exon 1A | 141 bp | 1–141 |
| Exon 1B | 371 bp | 411–781 |
| Exon 1C | 139 bp | 411–549 |
| Exon 2 | 67 bp | 11210–11276 |
| Exon 3 | 140 bp | 11367–11506 |
| Exon 4 | 251 bp | 23849–24099 |
| Exon 5 | 142 bp | 26311–26452 |
| Exon 6 | 68 bp | 34557–34624 |
| Exon 7 | 221 bp | 36060–36280 |
| Exon 8 | 99 bp | 39773–39871 |
| Exon 9 | 87 bp | 40245–40331 |
| Exon 10 | 174 bp | 42082–42255 |
| Exon 11 | 119 bp | 43217–43335 |
| Exon 12 |  | 45459 - |
| A of ATG |  | 11420 |
| T of TAG |  | 45627 |
| AATTAA |  | 46612 |

[1]The positions of the 5' end and the 3' end of each Exon were counted from the transcription start site of Exon 1A being defined as position +1. Note that this differs from the numbering in SEQ ID NO: 17.

The protein encoding portions of the gene begin with the ATG codon at position +11,420 where translation initiates in Exon 3 followed by exons encoding the remainder of the protein until stopping at a TAG codon (position +45,627) in Exon 12. 983 bp downstream from this TAG stop codon lies the putative polyadenylation signal AATTAA at position +46,612. Interestingly, the intron between Exon 1 and Exon 2 is about 10 kBp, between Exon 3 and Exon 4 is about 12 kBp and between Exon 5 and Exon 6 is about 8 kBp. The entire mouse PS-1 gene sequence is set forth as SEQ ID NO: 17 herein, but with exon 1A beginning at nucleotide 2234. Note in SEQ ID NO: 17 that the A's of the start codons for all the transcripts, i.e., A,B, and C are at the same position, 13653 in exon #, T's of the stop codons for all the transcripts are at the same position, 47860 in exon 12, and the polyadenylation signals for all the transcripts are at the same position, 48845, So the translations for all the transcripts are the same.

Characterization of the Mouse Presenilin-1 Promoter:— 2300 bp of DNA sequence located upstream of the +1 initiation of transcription site for Transcript A was compared to its human PS-1 genomic DNA counterpart (FIG. 3). The region of maximal similarity with human extends from positions −39 to +117 in the mouse sequence. This region is rich in Guanosine (G) and Cytosine (C) residues and contains the sequence motifs GCCGGAAGT (SEQ ID NO: 11) resembling an Ets 1–3 element (Fisher, R. et al., Oncogene 6, 2249–2254 (1991)) and a GGGCGGG (SEQ ID NO: 12) motif resembling an Sp-1 hexanucleotide element commonly found in the promoters of other genes. The mouse sequences upstream of this region do not share similarity with the human sequence nor do they contain the most common eucaryotic promoter element, a TATA box (FIG. 4). Instead, this unique mouse sequence contains two CAAATA motifs at positions −365 and −281 which resemble CAAT boxes found in other eucaryotic promoters. This unique region also contains an Ap-2 binding element at position −80 (CCCAGCCC) (SEQ ID NO: 13) and a sequence similar to a heat shock inducible element at position −220 (CTCGAATCGCAG) (SEQ ID NO: 14). Putative Sp-1 hexanucleotide binding sites with the sequence GGGCGG (SEQ ID NO: 15) or CCGCCC (SEQ ID NO: 16) are found downstream from the +1 site of transcription initiation with Exon IA containing one Sp1 motif and Intron 1A containing five motifs. Also downstream of the Cap (transcription initiation) site are two additional Ap-2 sites and another Ets 1–3 motif.

Figure 5A:
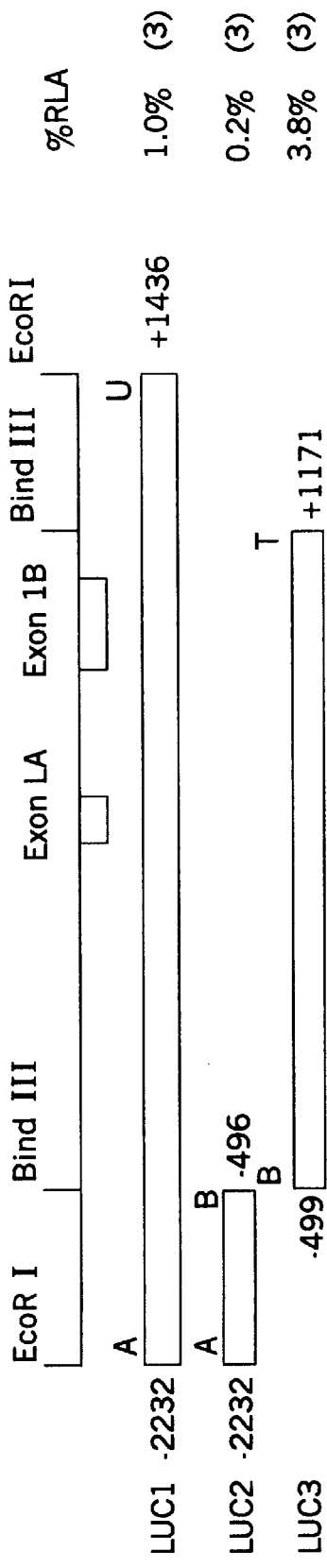
FIGS. 5A and 5B Mouse Presenlin-1 Promoter-Reporter Constructs and their Relative Luciferase Activity (%RLA).
Figure 5B:
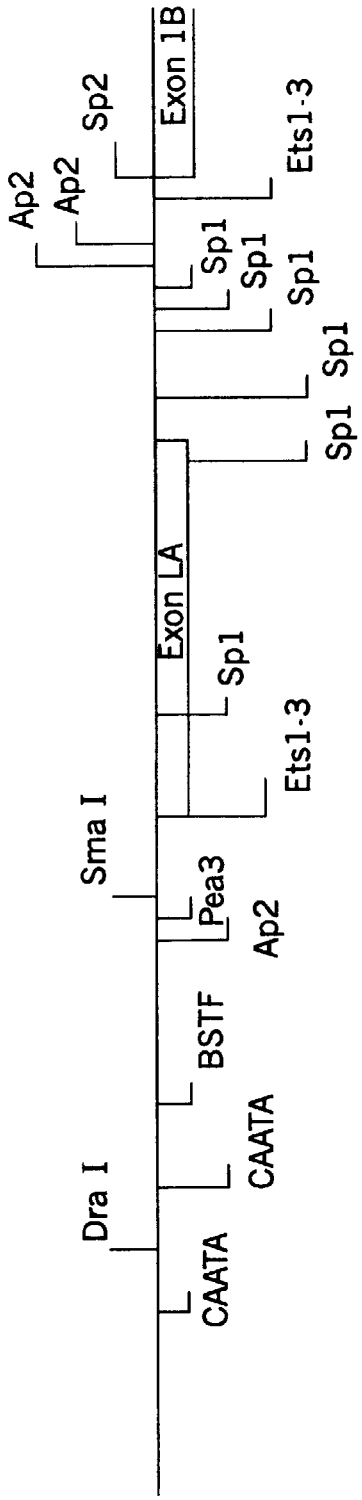
Figure 5C:
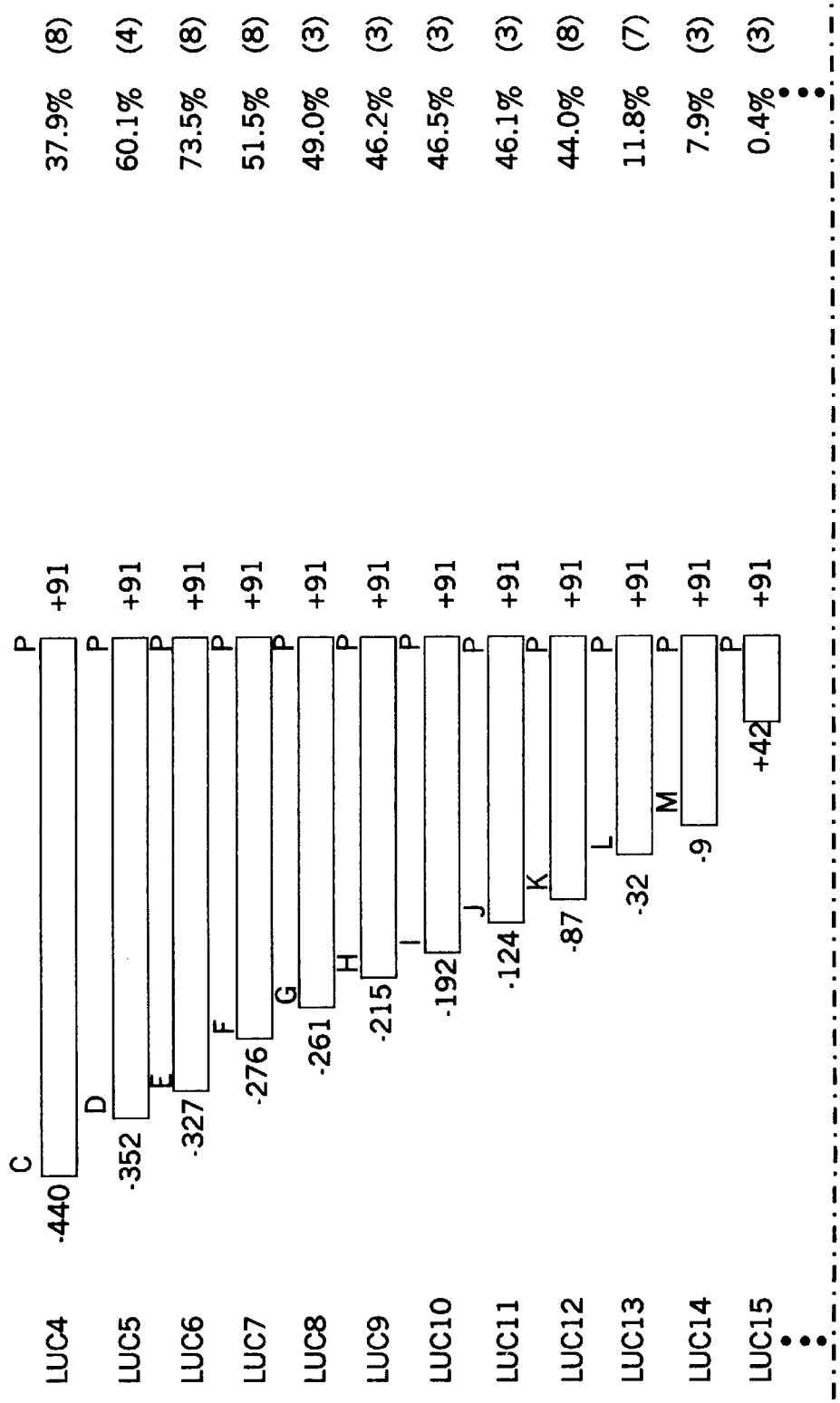

To test whether these elements function to promote transcription, we employed a Dual-Luciferase Reporter Assay System (Promega). In general, we assayed the promoter activity of DNAs flanking the transcription initiation site of PS-1 by inserting these DNA fragments in front of a basic, promoterless firefly Luciferase reporter gene in plasmid pGL3. Constant amounts of pGL3 containing PS-1 promoter fragments and of pRL-TK plasmid containing a Herpes Simplex Virus Thymidine Kinase (HSV-TK) promoter driving expression of sea pansy Luciferase were co-transfected into a constant number of cells. After 24 hours, lysates of transfected cells were sequentially assayed for firefly luciferase ($LA_F$) and sea pansy luciferase activity ($LA_R$) so that a ratio of firefly to sea pansy activities could be calculated for each PS-1 promoter fragment as its Relative-Luciferase-Activity or RLA. Of all the fragments tested, plasmid LUC 29 with the fragment −327 to +206 showed the greatest ratio of firefly to sea pansy activity (FIG. 5 and Table 2) which we defined as 100% activity. Larger fragments in LUC 1 (−2232 to +1436), LUC 3 (−499 to +1171) and LUC 16 (−276 to +519) display only a small percentage of the LUC 29 activity suggesting the presence of negative elements that apparently reduce their activities. Interestingly, the high activity of LUC 29 is not found in its flanking fragments such as LUC 2 (−2232 to −496) and LUC 23 (+188 to +519) which both lack significant promoter activity. The LUC 23 result is particularly interesting because the alternative transcription start site begins at position +411 of Exon 1B/Exon 1C and apparently lacks meaningful promoter activity.

TABLE 2

Neuron-Preferred Activity of Total and Core Promoter Regions of the Mouse PS-1 Gene.[2]

| Cell line | N2a | P19N | P19 | P19M | NIH/3T3 |
|---|---|---|---|---|---|
| Control | 2.1 | 10.6 | 5.0 | 35.9 | 1.1 |
| Luc29(total) | 36.8 | 114.1 | 21.2 | 114.9 | 0.3 |
| Luc27(core) | 3.6 | 11.5 | 3.7 | 19.4 | 0.1 |
| (IRLA)total | 17.8 | 10.8 | 4.3 | 3.2 | 0.3 |
| (IRLA)core | 1.7 | 1.1 | 0.7 | 0.5 | 0.1 |
| Total/core | 10.2 | 9.9 | 5.8 | 5.9 | 3.4 |

[2]LUC29 and LUC27 were transiently transfected into the cell lines to measure the activities of Total- and Core-promoter, respectively. An SV40-promoter driving Firefly luciferase in pGL3-Basic plasmid (Promega) was also transfected as a control. An index of relative luciferase activity (IRLA) was calculated for the Total- and the Core-promoter as IRLA = $RLA/RLA_{SV40}$.

To more accurately define the minimal or core regions conferring promoter activity, we studied the −327 to +206 region of the PS-1 gene in greater detail. Sequence comparision showed this region to contain a CAAT box (−281), a heat shock element (−220), an AP2 site (−80), a PEA-3 site (−53), an Ets 1–3 site (−7) and Sp1 sites (+25, +119 and +161). To find which of these elements and/or new elements were functionally active, we performed resection experiments to test smaller fragments within this region for promoter activity. Since LUC 24 and LUC 23 lacked significant activity, we initially focused on the fragments from −440 to +91 as shown in FIG. 4. The CAAT box at −281 plays an active role in the PS-1 promoter because LUC 8 (−261 to +91) has less activity than LUC 6 (−327 to +91) which contains this CAAT box. A negative element must reside upstream of this CAAT box because the activity of LUC 4 (−440 to +91) is about half that of LUC 6 (−327 to +91). The Heat Shock element at −220 may not play a role in PS-1 promoter activity as fragments containing (LUC 8, −261 to +91) and lacking (LUC 10, −192 to +91) this element have similar activities. The AP2 site at −80 and/or the PEA-3 site at −53 appear to play positive roles in PS-1 promoter function as LUC 12 (−87 to +91) has about four fold more activity than LUC 13 (−32 to +91) which lacks these sites. Similarly, the Ets 1–3 site at position −7 plays a positive role as judged by the RLA activity of LUC 14 (−9 to +91) at 7.9% and LUC 15 (+42 to +91) at 0.7%. While the Sp1 site at position +161 does not appear to contribute when LUC 17 (−276 to +206) is compared to LUC 18 (−276 to +148), the Sp1 sites at +25 and +119 appear to be very active in the PS-1 promoter as negative and positive elements, respectively, when LUC 26 (−9 to +41) is compared to LUC 27 (−9 to +16) and LUC 7 (−276 to +91) is compared to LUC 18 (−276 to +148).

Based on these experiments, we tested whether the region from −87 to +41 could contain the core promoter activity in two ways. First, LUC 25 (−87 to +41) had an RLA promoter activity of 28%. Second, the deletion of this region to give LUC 30 (delete −87 to +41 from −327 to +206) decreased activity from 100% (LUC 29) to 0.2% (LUC 30). Taken together, these results strongly suggest that the Ap2, PEA-3, Ets 1–3 and Sp1 elements comprise the major functional elements of the PS-1 promoter in the region −87 to +41.

Figure 6:
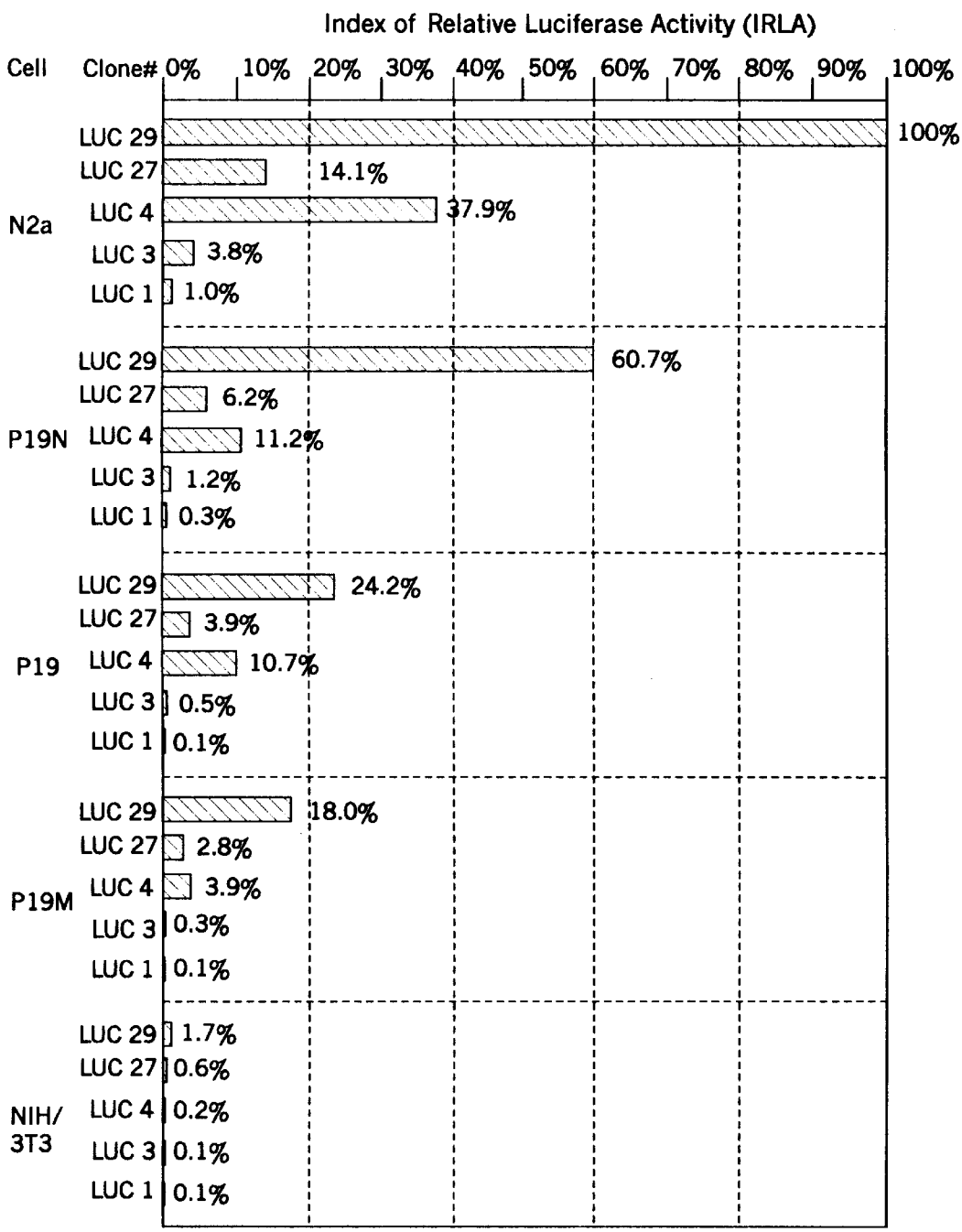
FIG. 6. Cell-Type Specific PS-1 Promoter Activity. PS-1 promoter-reporter constructs LUC 29, LUC 27, LUC 4, LUC 3 and LUC 1 were transiently transfected into Neuro2a-neuroblastoma (N2a), undifferentiated P19 (P19), retinoic acid differentiated neuron-like P19 (P19N), dimethylsulfoxide differentiated muscle-like P19 (P19M) and NIH/3T3-fibroblast cells. An SV40-promoter driving Firefly luciferase in pGL3-Basic plasmid (Promega) and pRL-TK (Thymidine Kinase promoter driving Renilla luciferase gene) was also transfected into each cell line as external and internal controls, respectively. After measuring luciferase activity from all combinations of plasmids, the Index of Relative Luciferase Activity (IRLA) was calculated as RLA/$RLA_{SV40}$, where $RLA_{SV40}$ is the ratio of Firefly luciferase signal in the external control divided by the Renilla luciferase signal in the internal control, as to compare the activity of different promoter fragments in different cell lines. Plasmid LUC 29 transfected into N2a cells showed the greatest IRLA value which we defined as 100% activity.

Cell-Specific Transcription:—Using in situ hybridization to human brain slices, we found that PS-1 RNA was most abundant in neurons and below the limits of detection in other brain cells. This result suggested that the PS-1 promoter may preferentially function in neurons. To test this idea further, we compared the activity of the promoter-fragment/reporter plasmids LUC 1, LUC 3, LUC 4, LUC 27 and LUC 29 in different cell types. As reported above, the mouse Neuro-2A cell line of neuroectodermal lineage supports more RLA promoter activity from LUC 29 and LUC 4 than from LUC 27, LUC 3 and LUC 1 (FIG. 6 and Table 2). In contrast, the mouse NIH/3T3 fibroblast cell line supports only minimal promoter activity with each of these promoter/reporter constructs (LUC 29, LUC 27, LUC 4, LUC 3 or LUC 1). To further test the idea that the PS-1 promoter activity is great in neurons, we transfected the mouse embryonal carcinoma cell line P19 with these reporter constructs. P19 cells are uniquely differentiated by retinoic acid treatment into a neuron-like phenotype (Jones-Villeneuve, E. et al., *Mol. Cell. Biol.* 3, 2271–2279 (1983)) or by dimethylsulfoxide treatment into a muscle-like phenotype (Edwards, M. et al., *Mol. Cell. Biol.* 3, 2280–2286 (1983).). Retinoic acid-treated P19 cells support as much as 2.5 fold more relative luciferase activity from plasmid LUC 29 compared to untreated P19 cells. Untreated P19 cells support as much as 1.3 fold more relative luciferase activity compared to dimethylsulfoxide-treated P19 cells Discussion From promoter to poly-adenylation signal, the full sequence of the mouse Presenilin-1 gene and its exon-intron structure set the stage to describe some of its unique functions. In contrast to the reported PS-1 cDNA sequence, 5' RACE (Rapid Amplification of cDNA Ends) surprised us by amplifying three different mRNA transcripts which share two unique transcription start sites. Sequence analysis showed that Transcript-A begins with Exon 1A while Transcript-B and Transcript-C begin with Exon 1B. Exon 1C is a fragment of Exon 1B sharing its 5' end at position +411, but only extending to position +549. This example of alternative splicing in Exon 1B versus Exon 1C to yield multiple RNA transcripts is well known in the field and has been described for Exon 9 in the human PS-1 gene (Perez-Tur, J. et al., *Neuroreport.* 7, 297–301 (1995)). Two distinct transcription start sites, however, have been reported for only a few genes including human catechol-O-methyl transferase (Tenhunen, J. et al., *Eur. J Biochem.* 223, 1049–1059 (1994)), mouse Neurotrophin-3 (Leingartner, A. et al., *Eur. J. Neurosci.* 223, 1149–1159 (1994)) and rat aromatic L-amino acid decarboxylase (Albert, V. et al., *Proc. Natl. Acad. Sci. U. S. A.* 89, 2053–12057 (1992)). In these cases, each transcriptional start site was associated with a distinct promoter so that a stoichiometry of one promoter per transcription start site was observed.

Our characterization of promoter activities for the PS-1 gene, however, revealed a much different picture. Using a promoter-fragment coupled to the Firefly luciferase reporter with sea pansy Renilla luciferase as an internal standard, we found that the −327 to +206 fragment (LUC 29) contains most of the PS-1 promoter activity. The known sequence motifs which apparently contain this activity are a CAAT box (−281), an Ap2 site (−80), a PEA-3 site (−53), an Ets 1–3 site (−7) and an Spl site (+25). While this region overlaps some of Exon 1A, deletion of the −87 to +41 region in LUC 30 reduces promoter activity by 50 fold. For the alternative transcription start site at position +410 in Exon 1B and Exon 1C, we tested LUC 23 (+118 to +519) containing Sp1, Ap2 and Ets 1–3 sites and found it to display about 1% of the activity surrounding the Exon 1A promoter. These results suggest to us that the region surrounding the +1 position of Exon 1A may promote the expression of Transcript-A, Transcript-B and Transcript-C. Alternatively, a weak promoter controlling transcription initiation at position +410 in Exon 1B/Exon 1C may amount to only 1% of the transcription initiation at position +1. By cloning all of the products of the 5' RACE into plasmid vectors and counting the number of clones carrying Exon 1C, we estimate the abundance of Transcript-C to approach 30% of all of the PS-1 transcripts (data not shown) further supporting the idea that the major promoter at +1 functions to control transcription initiation from both the +1 and the +410 sites. Quantitative measurement of Transcript-A, Transcript-B and Transcript-C levels will help to further resolve this issue. The high homology between human and mouse promoters, combined with our description of multiple start sites and alternative splicing for the mouse PS-1 gene, reasonably suggests how the human PS-1 promoter may function (FIG. 6).

Recently, PS-1 was reported to be expressed predominantly in neurons of the central nervous system (Kovacs, D. et al., *Nat. Med.* 2, 224–229 (1996)). This result matches our own data that PS-1 RNA, by in situ hybridization, is strongly expressed in neurons and at undetectable levels in other cell types. Similarly, several immunohistochemical studies report primarily neuronal localization of PS-1 protein with weak staining of amyloid plaques and some glia surrounding those plaques. On the other hand, Sherrington et al. showed that Northern blots of RNA from different organs all hybridized to a PS-1 cDNA probe suggesting that PS-1 RNA is ubiquitously expressed. At present, these results can not be easily reconciled.

Our data shows preferential promoter activity in neuron-like cells supporting a cell-type-specific pattern of PS-1 expression. We find the greatest amount of PS-1 promoter activity in the mouse Neuro2a-neuroblastoma cell line, followed by the P19 embryonal carcinoma cell line and almost no activity in the mouse NIH/3T3 fibroblast cell line (Table 2). To further confirm this finding, we employed the P19 mouse embryonal carcinoma cell line because of its unique ability to be differentiated into a muscle-like phenotype (aka. P19-DMSO-muscle) following dimethylsulfoxide treatment or into a neuron-like phenotype (aka. P19-RA-neuron) following all trans-retinoic acid treatment (Jones-Villeneuve, E. et al., *Mol. Cell. Biol.* 3, 2271–2279 (1983); Edwards, M. et al., *Mol. Cell. Biol.* 3, 2280–2286 (1983)). If our hypothesis that PS-1 promoter activity is preferred in neuron-like cells, then we would predict that P19 cells differentiated with retinoic acid into neuron-like cells would display more PS-1 promoter activity than P19 cells differentiated with dimethylsulfoxide into muscle-like cells. As clearly shown in FIG. 5 and Table 2, P19-RA-neuron cells display the most PS-1 promoter activity followed by untreated P19 cells and the least activity in P19-DMSO-muscle cells. These results combined with the Neuro2a and NIH/3T3 results indicate a clear pattern of PS-1 promoter activity which is preferred in neurons.

The mechanisms controlling neuron-specific promoter activity are poorly understood. The most direct mechanism would be for a positive regulator, that is only present in neuronal cells, to singularly activate the neuron-specific promoter. Alternatively, a negative regulator, that is only present in non-neuronal cells, could globally repress the neuron-specific promoter in all but neuronal cells. Depending upon the exact DNA elements within the promoter, some combination of positive and negative controls of transcriptional activity might also yield neuron-preferred promoter function. Going beyond our characterization of the regions conferring PS-1 promoter activity in Neuro2a cells, we may now look at the data to suggest which of the DNA elements might confer neuron-preferred promoter function. The region showing the highest activity in Neuro2a neuron-like cells extends from −329 to +206 (LUC 29) and contains a CAAT box at −281, a heat-shock inducible element at −218, an Ap2 site at −80, a PEA-3 site at −53, an Ets 1–3 site at −7 and an Sp1 site at +25. The CAAT box probably supports about a third of the positive control of neuron-specific activity as its deletion reduces promoter activity by about a third when comparing LUC 6 (−327 to +91) with LUC 8 (−261 to +91, FIG. 4). The heat shock element probably does not contribute to neuron-specific activity under normal conditions (non-stressed) as its deletion does not affect promoter activity when comparing LUC 8 (−261 to +91) to LUC 10 (−192 to +91, FIG. 4). Based on the four fold greater activity of LUC 12 (−87 to +91) compared to LUC 13 (−32 to +91), it appears that both the Ap2 site and the PEA-3 site are good candidates for the positive control of neuron-specific promoter function. Ap2 sites are reported to be most frequently found in promoters active in cells of neural crest lineage and several examples exist of their involvement with neuron-specific activity (Sato, T. et al., *J. Biol Chem.* 270, 10314–10322 (1995); Petersohn, D. et al., *J. Biol. Chem.* 270, 24361–24369 (1995); Chin, L. et al., *J. Biol. Chem.* 269, 18507–18513 (1994)). In contrast, the five fold less activity of LUC 26 (−9 to +41) compared to LUC 27 (−9 to +16) implicates the Sp1 site at +25 as a negative regulator of neuron-specific promoter function. These same data could also be interpreted as the Ets 1–3 site having a positive function, possibly as part of a core promoter element from −9 to +16. Direct measurement of LUC 27 (−9 to +16) shows that Neuro2a and P19-RA-neuron cells have more activity than do P19-DMSO-muscle or NIH/3T3 non-neuronal cells supporting the idea that this 25 bp region contributes to neuron-preferred promoter activity. The major transcription start site at position +1 is located in this proposed core promoter element. The ETS-1 transcription factor prefers binding to the Ets 1–3 binding site found in this core by a ratio of five to one over the PEA-3 binding site (Fisher, R. et al., *Oncogene* 6, 2249–2254 (1991)). This finding is particularly interesting as the ETS-1 transcription factor is thought to be specific for B cells and resting T cells of the immune system and not been previously described for neuronal cells. Sp1 binding sites appear to be ubiquitously distributed in all promoters of all cell types and their ability to function as negative elements appears to be novel.

The foregoing is illustrative of the present invention, and is not to be construed as limiting thereof. The invention is defined by the following claims, with equivalents of the claims to be included therein.

That which is claimed is:

1. An isolated mammalian Presenilin-1 gene promoter sequence that directs neuron-specific transcription of a downstream heterologous DNA sequence in a mammalian cell, the isolated promoter having a sequence selected from the group consisting of:

(a) the sequence spanning position 1906 to position 2027 of the mouse genomic Presenilin-1 gene of SEQ ID NO:17;

(b) the sequence spanning position 1784 to position 3404 of the mouse genomic Presenilin-1 gene of SEQ ID NO: 17;

(c) the sequence spanning position 2224 to position 2249 of the mouse genomic Presenilin-1 gene of SEQ ID NO:17; and (d) mammalian Presenilin-1 gene promoter sequences that hybridize to the isolated promoter sequence of (a), (b), or (c) above under conditions defined by a wash stringency of 0.3M NaCl, 0.03 M sodium citrate, and 0.1 % SDS at 60° C., and which promoter sequences when coupled to a downstream heterologous DNA sequence direct neuron specific transcription of said downstream heterologous DNA sequence in a mammalian cell.

2. An isolated DNA sequence having the sequence of the mouse Presenilin-1 gene promoter of SEQ ID NO: 17 from position 1906 to 2439.

3. A DNA construct comprising an expression cassette, which expression cassette comprises, in the 5' to 3' direction, the promoter sequence of (a), (b), (c), or (d) of claim 1, and a heterologous DNA sequence positioned downstream from the promoter sequence and operatively associated therewith.

4. The DNA construct according to claim 3, wherein said construct comprises a plasmid.

5. The DNA construct according to claim 3, wherein said heterologous DNA sequence encodes a protein.

6. An isolated cell containing the DNA construct according to claim 3.

7. A gene transfer vector comprising the DNA construct according to claim 6.

8. An isolated DNA sequence having the sequence of a mouse Presenilin-1 gene promoter of SEQ ID NO: 17 from position:

1799 to 2324;
   1881 to 2324;
   1906 to 2324;
   1954 to 2324;
   1972 to 2324;
   2018 to 2324;
   2041 to 2324;
   2109 to 2324;
   2146 to 2324; or
   2201 to 2324.

9. An isolated DNA sequence having the sequence of a mouse Presenilin-1 gene promoter of SEQ ID NO: 17 from position:

1954 to 2752;
   1954 to 2439;
   1954 to 2381; or
   1954 to 2274.

10. An isolated DNA sequence having the sequence of a mouse Presenilin-1 gene promoter of SEQ ID NO: 17 from position:

2146 to 2264;
   2224 to 2249; or
   1906 to 2499.

* * * * *